United States Patent
Chadwick et al.

(10) Patent No.: US 7,304,073 B2
(45) Date of Patent: Dec. 4, 2007

(54) METHOD OF TREATING MYOCARDIAL ISCHEMIA-REPERFUSION INJURY USING NF-KB INHIBITORS

(75) Inventors: Christopher Cyril Chadwick, West Chester, PA (US); Douglas Carl Harnish, Pennsburg, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/206,233

(22) Filed: Aug. 17, 2005

(65) Prior Publication Data

US 2006/0111421 A1 May 25, 2006

Related U.S. Application Data

(60) Provisional application No. 60/603,216, filed on Aug. 20, 2004.

(51) Int. Cl.
*A61K 31/473* (2006.01)
(52) U.S. Cl. ..................... 514/298; 546/108
(58) Field of Classification Search .............. 514/298; 546/108
See application file for complete search history.

(56) References Cited

U.S. PATENT DOCUMENTS

| | | | |
|---|---|---|---|
| 5,877,169 A | 3/1999 | Simpkins | 514/179 |
| 6,326,365 B1 | 12/2001 | Simpkins et al. | 514/179 |
| 6,339,078 B1 | 1/2002 | Simpkins et al. | 514/179 |
| 6,350,739 B1 | 2/2002 | Simpkins et al. | 514/182 |
| 6,894,061 B2 * | 5/2005 | Molinari et al. | 514/298 |
| 2005/0113405 A1 * | 5/2005 | Harnish et al. | 514/298 |
| 2005/0119276 A1 * | 6/2005 | Harnish et al. | 514/255.01 |
| 2005/0119324 A1 * | 6/2005 | Harnish et al. | 514/406 |

OTHER PUBLICATIONS

Delyani et al. J. Mol. Cell Cardiol. 28, 1001-1008 (1996).*
Boden E. P. et al., "Proton-Transfer Steps in Steglich Esterification: A Very Practical New Method for Macrolactonization," *J. Org. Chem*, 1985, 50, 2394-2395.
Delyani, J. A. et al., "Protection from myocardial reperfusion injury by acute administration of 17β-estradiol," *J. Mol. Cell Cardiol.* 1996, 28,1001-1008.
Hale, S.L. et al., "β-estradiol, but not α-estradiol, reduces myocardial necrosis in rabbits after ischemia and reperfusion," *Am. Heart J.* 1996,132, 258-262.
Huang J. et al., "Efficient Cross-Coupling of Aryl Chlorides with Aryl Grignard Reagents (Kumada Reaction) Mediated by a Palladium/Imidazolium Chloride System," *J. Am. Chem Soc.*, 1999, 121, 9889-9890.
Hulley, S. et. al., "Randomized Trial of Estrogen Plus Progestin for Secondary Prevention of Coronary Heart disease in Postmenopausal Women," *J. Am. Med. Assoc.*, 1998, 280(7), 605-613.
Kim, Y. D. et al., "17β-estradiol prevents dysfunction of canine coronary endothelium and myocardium and reperfusion arrhythmias after brief ischemia/reperfusion," *Circulation* 1996, 94(11), 2901-2908.
Krishnan, R. et al., "Reactions of Hydroxybenzophenone with Hydrazines," *J. Heterocycl. Chem*, 1988, 25, 447-452.
Li, H. Y. et al., "Enhanced responses to 17β-estradiol in rat hearts treated with isoproterenol: Involvement of a cyclic AMP-dependent pathway," 2000, *J. Pharmacol. Exp. Ther.* 293(2), 592-598.
Lucchesi, B. R., "Myocardial reperfusion injury—Role of free radicals and mediators of inflammation," in *Heart Physiology and Pathophysiology*, 4th ed. Chapter 65, pp. 1181-1220, Academic Press (2001).
*March's Adv. Org. Chem*, 5th ed, 16: 1183, Wiley Interscience, 2001.
Miyaura, N. et al., "Palladium-Catalyzed Cross-Coupling Reactions of Organoboron Compounds," *Chem Rev.*, 1995, 95, 2457-2483.
Node, K. et al., "Roles of NO and $Ca^{2+}$-activated $K^+$ channels in coronary vasodilation induced by 17β-estradiol in ischemic heart failure," *FASEB J.* 1997, 11, 793-799.
Pfeffer, M. A. et al., "Myocardial infarct No one size fits all," *Circulation*, 2002, 105, 2577-2579.
Robertson et.al., "Synthesis and biochemical evaluation of tritium-labeled 1-methyl-N-(8-methyl-8-azabicyclo[3.2.1]oct-3-yl)-1H-indazole-3-carboxa mide, a useful radioligand for 5HT3 receptors," *J. Med. Chem.*, 1990, 33, 3176-3181.
Rodriguez, M. J. et al., "The Synthesis of Water Soluble Prodrugs Analogs of Echinocandin B," *Bioorg. Med. Chem. Lett.*, 1999, 9, 1863-1868.

* cited by examiner

*Primary Examiner*—Kamal A. Saeed
*Assistant Examiner*—Yong Chu
(74) *Attorney, Agent, or Firm*—Daniel Klein

(57) ABSTRACT

The present invention concerns a method of treatment or prevention of myocardial ischemia-reperfusion injury by diagnosing that a person is in need of treatment or prevention of myocardial ischemia-reperfusion injury and administering a therapeutically effective amount of a ligand which modulates NF-kB transcription factor by interaction with estrogen receptor ER-α, estrogen receptor ER-β, or both ER-α and ER-β estrogen receptors with a substantial absence of creatine kinase stimulation. In certain preferred embodiments, the administration is substantially without uterotropic activity.

9 Claims, 6 Drawing Sheets

US 7,304,073 B2

METHOD OF TREATING MYOCARDIAL ISCHEMIA-REPERFUSION INJURY USING NF-KB INHIBITORS

CROSS-REFERENCE TO RELATED APPLICATIONS

The present application claims benefit to U.S. Provisional Application Ser. No. 60/603,216, filed Aug. 20, 2004, which is incorporated herein by reference in its entirety.

FIELD OF THE INVENTION

This invention relates to methods of treatment or prevention of myocardial ischemia-reperfusion injury by modulating NFkB transcription with ligands that interact with the estrogen receptor, preferably in the absence of classic estrogenic activity.

BACKGROUND OF THE INVENTION

Cardiovascular disease is the leading cause of death in the western world. Coronary artery disease can lead to prolonged or irreversible episodes of cardiac ischemia that result in myocardial infarction (MI) which is associated with a high rate of mortality. See Lucchesi, *Myocardial reperfusion injury—Role of free radicals and mediators of inflammation. in: Heart Physiology and Pathophysiology,* 4th ed. Chapter 65, pp 1181-1220, Academic Press (2001); Pfeffer & McMurray, *Circulation* 2002, 105, 2577-2579.

Ischemia is an acute condition that results from insufficient flow of oxygenated blood to a part of the body. The reduced flow is typically caused by blockage of a vessel by an embolus (blood clot); the blockage of a vessel due to atherosclerosis; the breakage of a blood vessel (a bleeding stroke); the blockage of a blood vessel due to vasoconstriction such as occurs during vasospasms and possibly, during transient ischemic attacks (TIA) and following subarachnoid hemorrhage. Conditions in which ischemia occurs further include myocardial infarction; trauma; and during cardiac and thoracic surgery and neurosurgery (blood flow needs to be reduced or stopped to achieve the aims of surgery). Procedures that can cause ischemia include coronary thrombolysis, coronary angioplasty (with or without stent placement), and coronary artery bypass grafts. During myocardial infarct, stoppage of the heart or damage occurs which reduces the flow of blood to organs, and ischemia results. Cardiac tissue itself is also subjected to ischemic damage. During various surgeries, reduction of blood flow, clots or air bubbles generated can lead to significant ischemic damage.

During an ischemic event, there is a gradation of injury that arises from the ischemic site. Cells at the site of blood flow restriction, undergo necrosis and form the core of a lesion. A penumbra is formed around the core where the injury is not immediately fatal but progresses slowly toward cell death. This progression to cell death may be reversed upon reestablishment of blood flow within a short time of the ischemic event.

Use of an estrogen compound such as 17α-estradiol or 17β-estradiol, has been reported to be useful in the prevention and treatment of ischemic damage. See, U.S. Pat. Nos. 6,350,739; 6,339,078; 6,326,365; 5,877,169; Delyani et al., *J. Mol. Cell Cardiol.* 1996, 28, 1001-1008; Hale, et al., *Am. Heart J.* 1996, 132, 258-262; Kim, et al., *Circulation* 1996, 94, 2901-2908; Li et al., 2000, *J. Pharmacol Exp. Ther.* 293, 592-598; Node, et al., *FASEB J.* 1997, 11, 793-799.

17-β-Estradiol, however, strongly stimulates creatine kinase expression as well as proliferative effects on uterine and breast tissue. Thus, in ERT some potential unwanted side effects, such as an increase risk of cardiovascular events in the first year of use, have been demonstrated (Hulley, S. et. al., *J. Am. Med. Assoc.,* 1998, 280, 605) as well as proliferative effects on uterine and breast tissue. Ligands that exhibit the benefit of ERT without the unwanted side effects have been the subject of recent publications.

Current therapies including the use of vasodilators, anti-thrombotics/thrombolytics, β-blockers and coronary artery bypass graft are used pre and post MI to maintain/restore coronary blood flow and limit oxygen demand. However, there is an unmet need for therapies that can be used to directly inhibit the development of permanent cardiac injury during a myocardial infarction.

SUMMARY OF THE INVENTION

The present invention concerns methods of treating or preventing myocardial ischemia injury comprising administering a therapeutically effective amount of a ligand which modulates NF-kB transcription factor by interaction with estrogen receptor ER-α, estrogen receptor ER-β, or both ER-α and ER-β estrogen receptors, preferably with a substantial absence of creatine kinase stimulation. In certain preferred embodiments, the administration is with a substantial absence of uterotropic activity. Some preferred ligands interact with both ERα and ERβ receptors.

DETAILED DESCRIPTION OF ILLUSTRATIVE EMBODIMENTS

Figure 1:
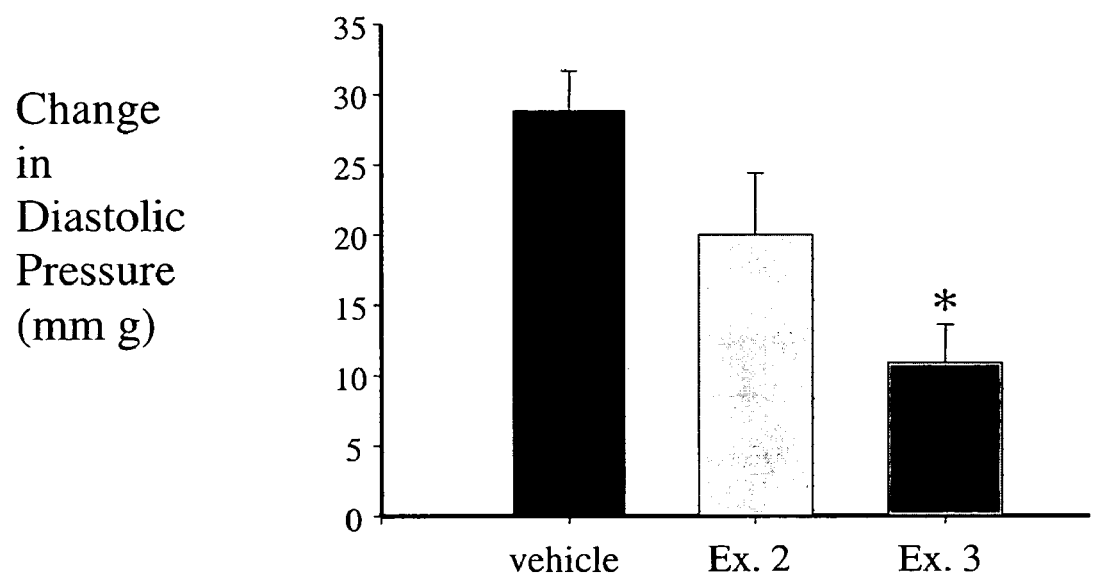
FIG. 1 shows the effect of the compounds of examples 2 and 3 on the increase in left ventricular diastolic pressure following ischemia-reperfusion. Values represent the mean±SEM. The compound of example 3 (n=8) treatment significantly attenuated the increase in diastolic pressure in comparison to vehicle treated hearts (n=17) following ischemia-reperfusion, *$p<0.01$.

The present invention provides methods for the treatment or prevention of myocardial ischemia injury. Compounds useful in the present invention preferably block interleukin-1β (IL-1β) induced nuclear factor kB (NF-kB) luciferase reporter activity or interleukin-6 (IL-6) expression in an ER dependent fashion in human endothelial cells. Particularly preferred ligands are devoid of the proliferative effects on uterine and breast tissue associated with estrogen in vivo as well as a lack of expression of creatine kinase (CK); a classic estrogen responsive gene in vitro. The selective anti-inflammatory compounds described herein are expected to prove useful for the treatment and prevention of chronic inflammatory diseases without stimulating uterine and breast cell proliferation as found with classic estrogens.

One family of compounds useful in the instant invention are substituted 4-(1H-indazol-3-yl)phenols represented by the general formula I and substituted 4-(2H-indazol-3-yl)phenols represented by formula II.

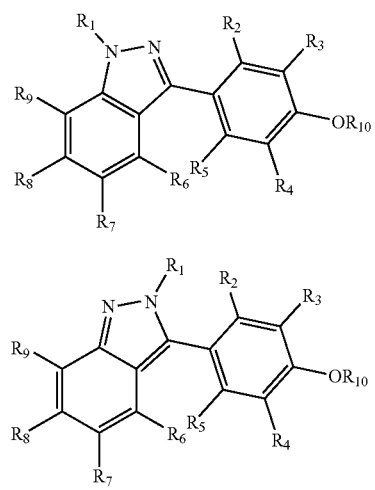

wherein:
$R_1$ is hydrogen, alkyl, alkenyl, cycloalkyl, cycloalkenyl, aryl, arylalkyl, or a heterocyclic ring system of 4-14 atoms, containing 1-4 heteroatoms selected from N, O, and S;

$R_2$, $R_3$, $R_4$, and $R_5$, are each, independently, hydrogen, alkyl, alkenyl, hydroxy, alkoxy, aryloxy, halogen, trifluoromethyl, —CN, —NO$_2$, —CHO, or —CO$_2$R$_{11}$;

$R_6$, $R_7$, $R_8$, and $R_9$, are each, independently, hydrogen, alkyl, alkenyl, hydroxy, alkoxy, aryloxy, halogen, trifluoromethyl, —CO$_2$R$_{11}$, aryl, arylalkyl, or a heterocyclic ring system of 4-14 atoms, containing 1-4 heteroatoms selected from N, O, and S;

$R_{10}$ is hydrogen, —CO$_2$R$_{11}$, —CONHR$_{11}$, —P(=O)(OH)OR$_{11}$, or —CO(CH$_2$)$_n$CH(NHR$_{12}$)CO$_2$R$_{11}$;

$R_{11}$ is hydrogen, alkyl, aryl, or arylalkyl;

$R_{12}$ is hydrogen or —CO$_2$R$_{11}$;

n=0-3, or a pharmaceutically acceptable salt thereof.

In some embodiments, $R_1$ is hydrogen, alkyl of 1-6 carbon atoms, alkenyl of 2-7 carbon atoms, cycloalkyl of 3-8 carbon atoms, cycloalkenyl of 4-8 carbon atoms, aryl of 6-20 carbon atoms, arylalkyl of 7-26 carbon atoms, or a heterocyclic ring system of 4-14 atoms, containing 1-4 heteroatoms selected from N, O, and S;

$R_2$, $R_3$, $R_4$, and $R_5$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CN, —NO$_2$, —CHO, or —CO$_2$R$_{11}$;

$R_6$, $R_7$, $R_8$, and $R_9$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CO$_2$R$_{11}$, aryl of 6-20 carbon atoms, arylalkyl of 7-26 carbon atoms, or a heterocyclic ring system of 4-14 atoms, containing 1-4 heteroatoms selected from N, O, and S; and $R_{11}$ is hydrogen, alkyl of 1-6 carbon atoms, aryl of 6-20 carbon atoms, or arylalkyl of 7-26 carbon atoms.

The compounds of formula I and formula II can be converted to salts, in particular pharmaceutically acceptable salts using art recognized procedures. The compounds of formulas I and II that have a basic center can form acid addition salts. These are formed, for example, with strong inorganic acids, such as mineral acids, for example sulfuric acid, phosphoric acid or a hydrohalic acid; with strong organic carboxylic acids, such as alkanecarboxylic acids of 1 to 4 carbon atoms which are unsubstituted or substituted, for example, by halogen; acetic acid; saturated or unsaturated dicarboxylic acids, for example oxalic, malonic, succinic, maleic, fumaric, phthalic, or terephthalic acid; hydroxycarboxylic acids, for example, ascorbic, glycolic, lactic, maleic, tartaric or citric acid; amino acids, for example aspartic or glutamic acid, or such as benzoic acid; or organic sulfonic acids, such as alkane- (of 1 to 4 carbon atoms) or arylsulfonic acids, for example, methane- or p-toluenesulfonic acid. Corresponding acid addition salts can also be formed having, if desired, an additionally present basic center. The compounds of formula I having at least one acid group can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds I or their pharmaceutically acceptable salts, are also included.

Some preferred 4-(1-H-indazol-3-yl)phenols useful in this invention include those of Group A in which:

$R_1$ is alkyl of 1-6 carbon atoms, alkenyl of 2-7 carbon atoms, cycloalkyl of 3-8 carbon atoms, cycloalkenyl of 4-8 carbon atoms, or a heterocyclic ring system of 4-14 atoms, containing 1-4 heteroatoms selected from N, O, and S;

$R_2$ is hydrogen, alkyl of 1-6 carbon atoms, alkenyl of 2-7 carbon atoms, hydroxy, alkoxy of 1-6 carbon atoms, or halogen;

$R_7$ and $R_9$, are each, independently, hydrogen, alkyl of 1-6 carbon atoms, hydroxy, halogen, trifluoromethyl, —$CO_2R_{11}$, aryl of 6-20 carbon atoms, arylalkyl of 7-26 carbon atoms, or a heterocyclic ring system of 4-14 atoms, containing 1-4 heteroatoms selected from N, O, and S, where the remaining substituents are as defined above.

Other preferred compounds of this invention include those of group B in which:

$R_1$ is alkyl of 1-6 carbon atoms, alkenyl of 2-7 carbon atoms, cycloalkyl of 3-8 carbon atoms, or cycloalkenyl of 4-8 carbon atoms;

$R_2$ is hydrogen, alkyl of 1-6 carbon atoms, halogen, or hydroxy;

$R_9$ is alkyl of 1-6 carbon atoms, halogen, trifluoromethyl, —$CO_2R_{11}$, aryl of 6-20 carbon atoms, arylalkyl of 7-26 carbon atoms, or a heterocyclic ring system of 4-14 atoms, containing 1-4 heteroatoms selected from N, O, and S;

$R_{10}$ is hydrogen;

where the remaining substituents are as defined above.

Yet other preferred compounds of this invention include those of C in which:

$R_1$ is alkyl of 1-6 carbon atoms or alkenyl of 2-7 carbon atoms;

$R_9$ is alkyl of 1-6 carbon atoms, halogen, or trifluoromethyl, where the remaining substituents are as defined above.

The reagents used in the preparation of the compounds of this invention can be either commercially obtained or can be prepared by standard procedures described in the literature. Compounds of formula I and formula II wherein $R_{10}$=H can be prepared from a common precursor of formula III as outlined in Scheme 1.

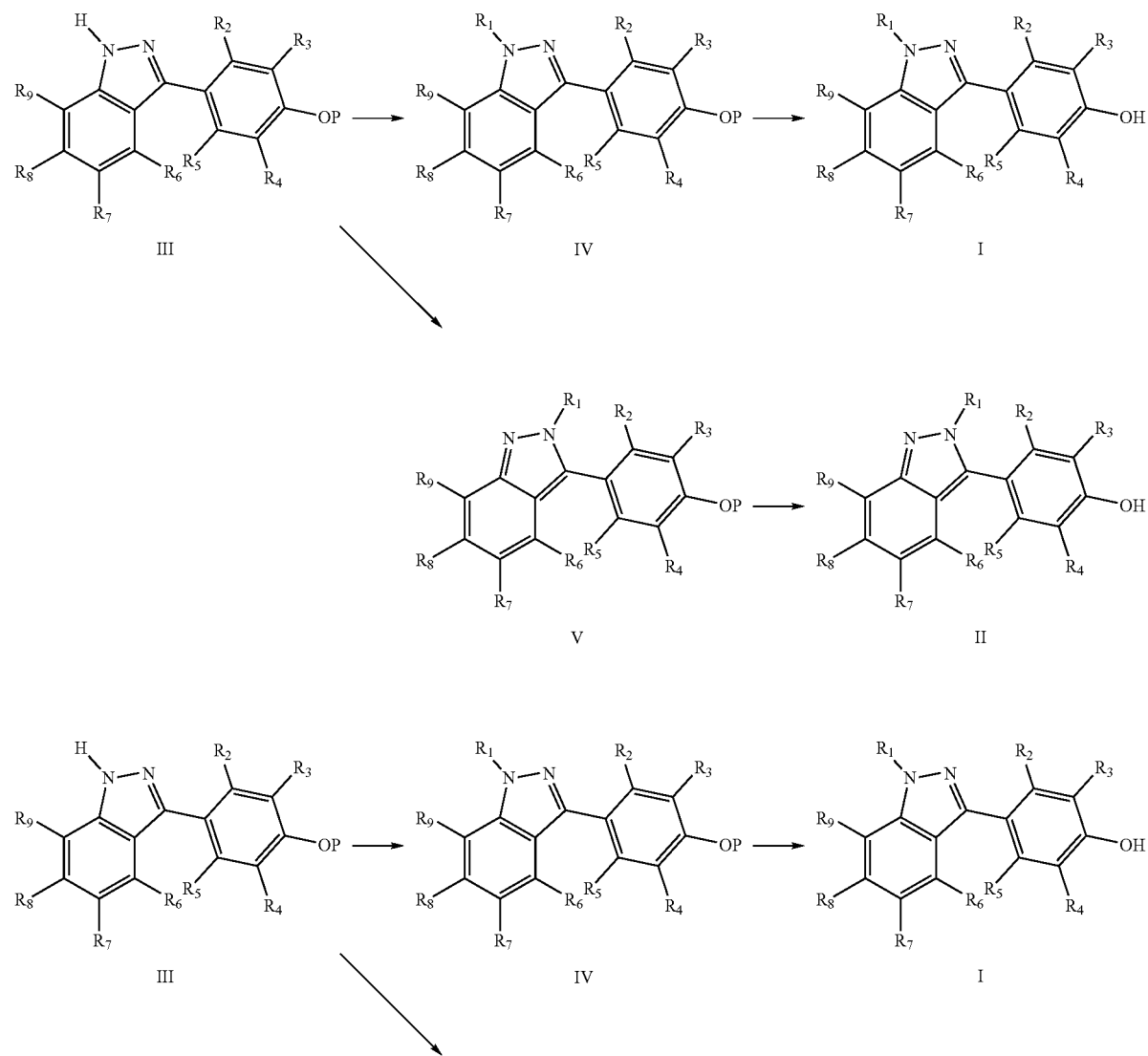

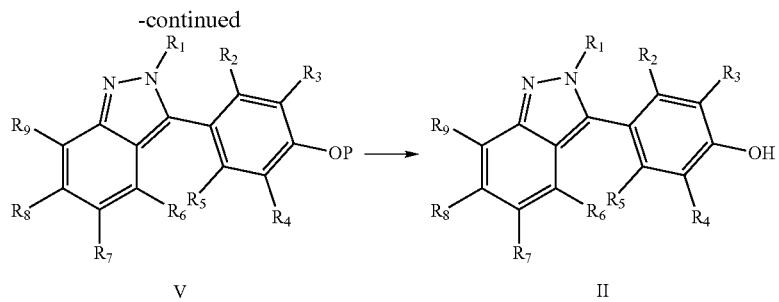

where
R$_1$ is alkyl, cycloalkyl, alkenyl, cycloalkenyl, alkyloxy;
R$_2$, R$_3$, R$_4$, R$_5$, R$_6$, R$_7$, R$_8$, and R$_9$ are as previously defined;
P is a phenol protecting group, preferably, but not limited to, methyl, benzyl or t-butyldiphenylsilyl.

Thus, compounds of formula III preferably are treated with sodium hydride in a suitable solvent such as 4-dimethylaminopyridine (DMAP). When the gas evolution ceases, the alkyl halide is added and the solution is heated at 50° C. overnight. The reaction is partitioned with ethyl acetate and water. The organic phase is dried with a suitable drying agent such as sodium sulfate (Na$_2$SO$_4$). The crude products IV and V are isolated as a single residue after filtration and concentration of the organic layer in vacuo. Separation is easily carried out by chromatography known to one skilled in the art, to provide the separated intermediates IV and V.

Compounds of formula I and formula II preferably are prepared from IV or V respectively by a deprotection step.

When P is benzyl, deprotection to the phenol preferably is accomplished by hydrogenation over 10% palladium on carbon using either hydrogen gas, or catalytic hydride transfer with cyclohexene or ammonium formate.

When P is methyl, deprotection preferably is carried out using BBr$_3$ with cyclohexene as a scavenger for HBr.

When P is t-butyldiphenylsilyl, deprotection can be accomplished with tetrabutylammonium fluoride.

Compounds of formula V can also be prepared as outlined in Scheme 2 from compounds of formula VI.

2-Fluorobenzophenones of compound VI can be reacted directly with optimally substituted hydrazines where R$_1$ is alkyl or aryl, which are either commercially available or readily prepared by common procedures known to those skilled in the art. Thus, a mixture of the benzophenones of compound VI are combined with the hydrazines in a suitable solvent such as methanol in the presence of ethyl acetate. The intermediate hydrazone either spontaneously cyclizes to the compounds of formula IV or can be isolated by concentration of the reaction mixture. The isolated hydrazone is heated neat to temperatures of up to 190° C. The residues are purified by chromatography to provide compounds of formula IV.

Compounds of formula I, wherein R$_2$ and R$_8$ are OH and R$_3$, R$_4$, R$_5$, R$_6$, R$_7$, and R$_9$ are hydrogen, can also be prepared by a similar process from commercially available 2,2′,4,4′-tetrahydrobenzophenone according to the literature preparation of R. Krishnan, S. A. Lang, Y. I. Lin, R. G. Wilkinson *J. Heterocycl. Chem,* 1988, 25, 447 and outlined in Scheme 3.

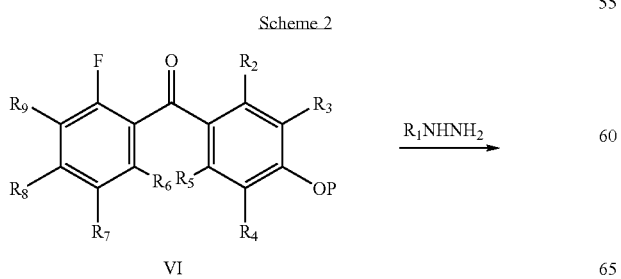

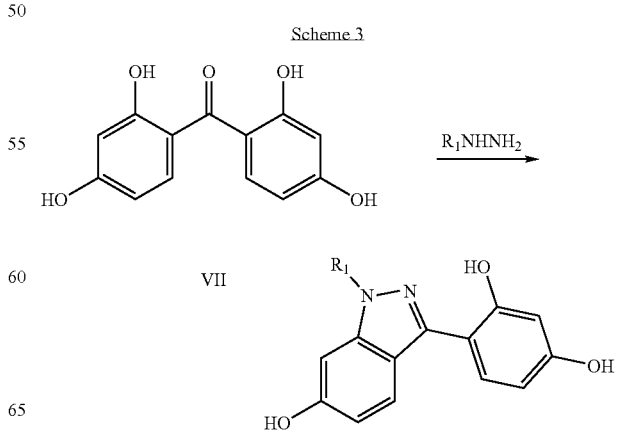

Thus, a solution of the substituted hydrazine salt (1 to 2 equivalents), sodium acetate (1 to 4 equivalents) and 2,2',4,4'-tetrahydroxybenzophenone (1 equivalent) in an appropriate solvent such as methanol (0.2 molar solution) is stirred at ambient temperature overnight. The reaction mixture is concentrated in vacuo and the residues partitioned with EtOAc and H$_2$O. The organic phase is dried (Na$_2$SO$_4$) and concentrated in vacuo to give the intermediate hydrazone. The residues are heated at 190° C. overnight. Product residues are purified by chromatography.

Compounds of formula III can be readily prepared from compounds of formula VI as shown in Scheme 4.

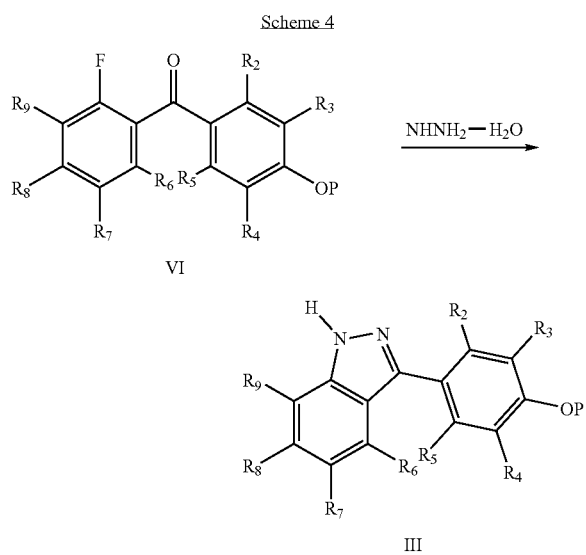

Thus, an appropriately substituted compound of formula VI is reacted with an excess of hydrazine hydrate in pyridine containing DMAP. The reaction is heated at 100° C. for at least 24 hours. The reaction is concentrated in vacuo and the residue is partitioned with ethyl acetate and 1 N HCl. The organic phase is washed with brine and dried with a drying agent such as Na$_2$SO$_4$. The solvent is evaporated to provide the compounds of formula III.

Compounds of formula VI can be readily prepared as outlined in Scheme 5 from the reaction of an appropriately substituted 2-fluoro-N-methoxy-N-methyl-benzamide of formula VII.

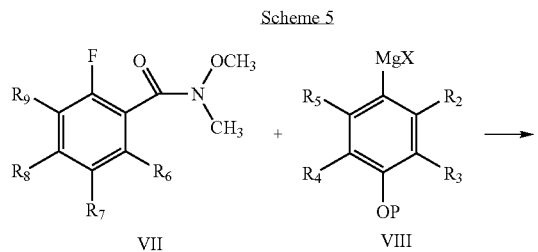

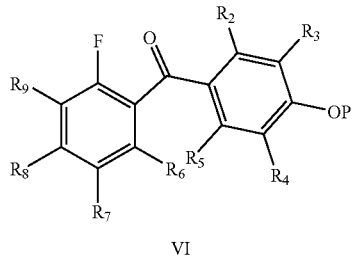

where X is preferably but not limited to Br. Compounds of formula VIII are either commercially available or readily prepared by one skilled in the art. One suitable solvent is tetrahydrofuran (THF).

The Weinreb amides of formula VII can are generated by the reaction of an appropriately substituted 2-fluorobenzoic acid with N,O-dimethylhydroxylamine and N,N-carbonyldiimidazole in a suitable solvent such as DMF (Robertson et. al., *J. Med. Chem.*, 1990, 33, 3167) or from the acid chloride prepared from reaction of the benzoic acid with oxalyl chloride in a suitable solvent such as THF in the presence of a base such as N,N-diisopropylethylamine.

Compounds of formula IV can also be prepared as outlined in Scheme 6

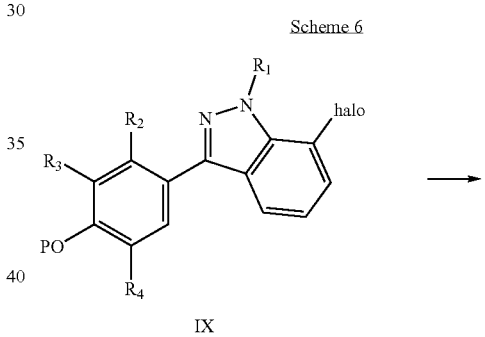

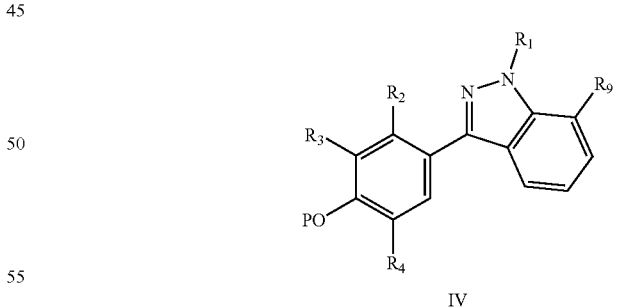

where
R$_1$, R$_2$, R$_3$, and R$_4$ are as defined above;
and halo is Cl or Br.

Thus, when halo is Br, compounds of formula IV where R$_9$ is aryl, heteroaryl, heterocycle, and alkenyl, can be prepared by the Suzuki coupling of IX with an appropriately substituted boronic acid in a suitable solvent such as dioxane, in the presence of an aqueous base such as potassium carbonate, in the presence of 1 to 5 mol % of palladium catalyst such as tetrakis(triphenylphoshine)palladium (0).

The mixture is typically heated at 80° C. for a period of 1 to 24 hours (see Miyaura, N. Suzuki, A., *Chem Rev.*, 1995, 95, 2457). The compounds are obtained in pure forms by chromatography known to those skilled in the art.

When halo is Cl, compounds of formula IV where $R_9$ is aryl, heteroaryl, heterocyclic can be prepared as described by Huang J. and Nolan S. P., et al, *J. Am. Chem Soc.*, 1999, 121, 9889. Thus, reaction of IX with a suitably substituted aryl magnesium bromide in a suitable solvent such as dioxane in the presence of an N-heterocyclic carbene ligand and a palladium catalyst such as but not limited to palladium (II)acetate.

Compounds of formula V can be prepared as outlined in Scheme 7.

-continued

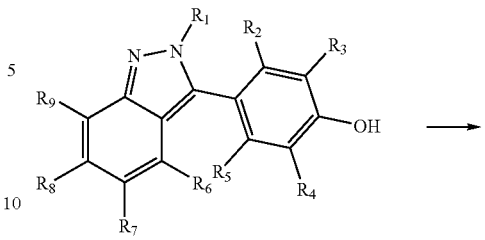

Scheme 7

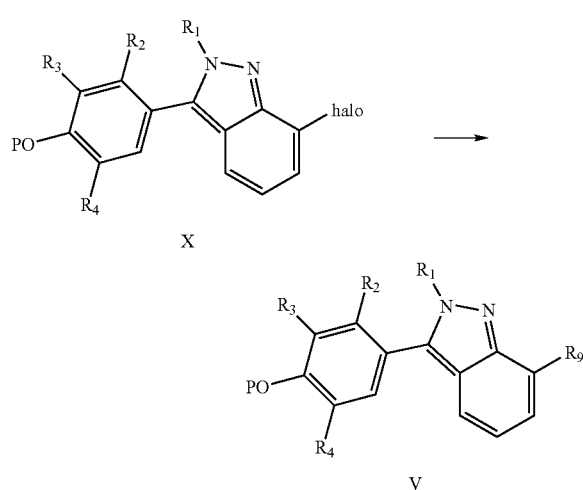

where $R_1$, $R_2$, $R_3$, and $R_4$ are as defined above; and halo is Cl or Br. Thus, compounds of formula V where $R_9$ is aryl, heteroaryl, heterocyclic, and alkenyl, can be prepared in an analogous fashion to the regioisomer described above in Scheme 6.

Prodrugs of formula I and formula II can readily be prepared as described below.

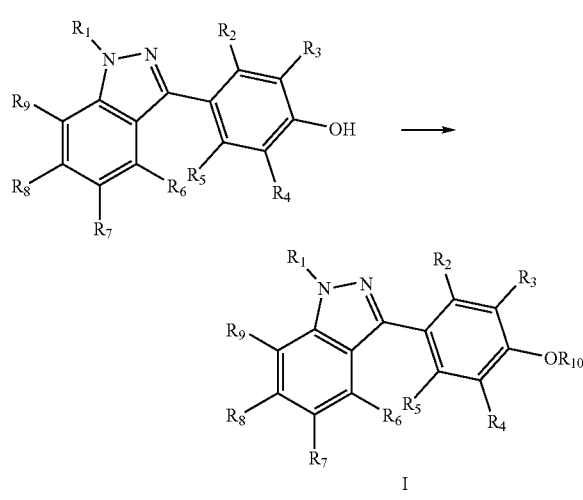

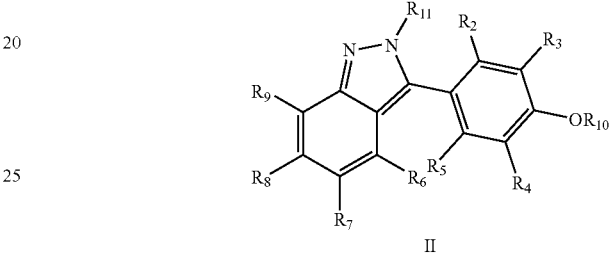

Thus when $R_{10}$ is $COOR_{11}$, compounds can be prepared by methods commonly known to those skilled in the art. The reaction of an acid chloride with compounds of formula I and formula II wherein $R_1$ is H in a suitable solvent such as methylene chloride in the presence of a suitable base such as N,N-diisopropylethylamine affords the ester prodrugs.

For amino acid esters, standard coupling techniques known to those skilled in the art can be used, including activation of the carboxylic acid in the presence of DMAP (Boden E. P., Keck, G. E., *J. Org. Chem*, 1985, 50, 2394). A solution of compounds of formulas I and II dicyclohexylcarbodiimide and DMAP in a suitable solvent such as $CH_2Cl_2$ is stirred overnight at ambient temperature. The reaction mixture is purified typically by column chromatography known to those skilled in the art to provide the ester.

When $R_{10}$ is $CONHR_{11}$, compounds of formula I and II may be reacted with substituted isocyanates in a suitable solvent such as dioxane and heated at 80° C. for up to 48 hours. (*March's Adv. Org. Chem*, 5$^{th}$ ed, 16: 1183, Wiley Interscience, 2001). When $R_{10}$ is $P(=O)(OH)OR_{11}$, the substituted hydrogen phosphates of compounds of formulas I and II can be prepared as described by Rodriguez, M. J. et al., *Bioorg. Med. Chem. Lett.*, 1999, 9, 1863. Thus, a solution of compounds of formulas I or II, wherein $R_{10}$ is H substituted dichlorophosphate and lithium hexamethyldisilazide in a suitable solvent such as THF is stirred for 1 hour at ambient temperature. The reaction mixture is quenched with $H_2O$ and purified by reversed phase HPLC, known by one skilled in the art.

Other useful compounds of the invention are dihydrophenanthridinesulfonamide compounds of formulae (XI) or (XII):

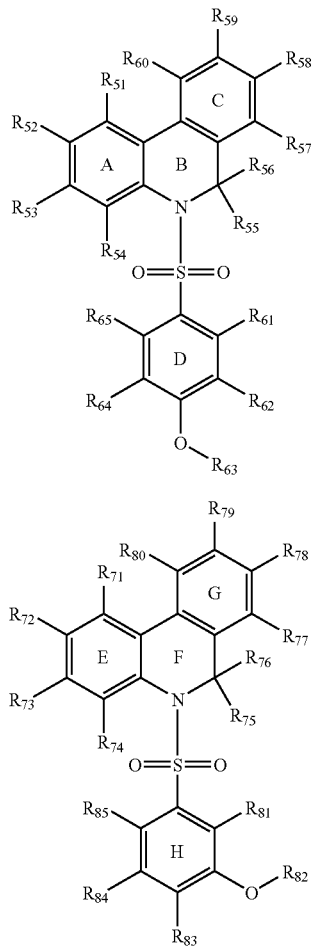

(XI)

(XII)

wherein $R_{51}, R_{52}, R_{53}, R_{54}, R_{57}, R_{58}, R_{59}, R_{60}, R_{61}, R_{62}, R_{64}$, and $R_{65}$ are each, independently, hydrogen, $R_{67}$, monofluoroalkyl, monofluoroalkenyl, aryl-$R_{66}$—, heteroaryl-$R_{66}$—, hydroxyalkyl, HO—$R_{66}$—, $R_{67}$—X—$R_{66}$—, HS—$R_{66}$—, $R_{67}$—S(O)—, $R_{67}$—S(O)$_2$—, $R_{67}$—SO$_3$—, $R_{67}$—S(O)$_2$NR'—, —N(R')$_2$, —NR'—C(NH$_2$)=NR', cyano, nitro, halogen, —OR', —SR', —SO$_3$R', —S(O)$_2$N(R')$_2$, —C(O)R', —C(R')=N—OR', —C(NH$_2$)=NR', —CO$_2$R', —OC(O)R', or —C(O)N(R')$_2$; or are linked with either $R_{p+1}$ or $R_{p-1}$ by an -alkylene-, or —X-alkylene-group;

$R_{55}$ is hydrogen, $R_{67}$, monofluoroalkyl, monofluoroalkenyl, aryl-$R_{66}$—, heteroaryl-$R_{66}$—, hydroxyalkyl, HO—$R_{66}$—, $R_{67}$—X—$R_{66}$—, HS—$R_{66}$—, —C(O)R', —CO$_2$R', or —C(O)N(R')$_2$; or $R_{55}$ may be linked with either $R_{56}$ or $R_{57}$ and linked with an -alkylene- or —X-alkylene-group;

$R_{56}$ is hydrogen, $R_{67}$, monofluoroalkyl, monofluoroalkenyl, aryl-$R_{66}$—, heteroaryl-$R_{66}$—, hydroxyalkyl, HO—$R_{66}$—, $R_{67}$—X—$R_{66}$—, HS—$R_{66}$—, —C(O)R', —CO$_2$R', or —C(O)N(R')$_2$; or $R_{66}$ may be linked with either $R_{55}$ or $R_{57}$ and linked with an -alkylene- or —X-alkylene-group;

$R_{63}$ is R', $R_{67}$—X—$R_{66}$—, $R_{67}$—S(O)—, $R_{67}$—S(O)$_2$—, —SO$_3$R', —S(O)$_2$N(R')$_2$, or D-glucuronidate;

$R_{66}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{67}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R' is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-(C$_2$-C$_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R' groups, the R' groups may be linked with an -alkylene- group;

X is O, —NR'—, —S(O)$_m$—, —C(O)—, —OC(O)—, —C(O)O—, —NR'C(O)—, or —C(O)NR'—;

m is 0, 1, or 2;

p is 52, 53, 56, 57, 58, 59, 62, 63, or 64;

$R_{71}, R_{72}, R_{73}, R_{74}, R_{77}, R_{78}, R_{79}, R_{80}, R_{81}, R_{83}, R_{84}$, and $R_{85}$ are, independently, hydrogen, $R_{67}$, monofluoroalkyl, monofluoroalkenyl, aryl-$R_{66}$—, heteroaryl-$R_{66}$—, hydroxyalkyl, HO—$R_{66}$—, $R_{67}$—Y—$R_{66}$—, HS—$R_{66}$—, $R_{67}$—S(O)—, $R_{67}$—S(O)$_2$—, $R_{67}$—SO$_3$—, $R_{67}$—S(O)$_2$NR'—, —N(R')$_2$, —NR'—C(NH$_2$)=NR', cyano, nitro, halogen, —OR', —SR', —SO$_3$R', —S(O)$_2$N(R')$_2$, —C(O)R', —C(R')=N—OR', —C(NH$_2$)=NR', —CO$_2$R', —OC(O)R', or —C(O)N(R')$_2$; or are linked with either $R_{q+1}$ or $R_{q-1}$ by an -alkylene-, or —Y-alkylene-group;

$R_{75}$ is hydrogen, $R_{67}$, monofluoroalkyl, monofluoroalkenyl, aryl-$R_{66}$—, heteroaryl-$R_{66}$—, hydroxyalkyl, HO—$R_{66}$—, $R_{67}$—Y—$R_{66}$—, HS—$R_{66}$—, —C(O)R', —CO$_2$R', or —C(O)N(R')$_2$; or $R_{25'}$ may be linked with either $R_{76}$ or $R_{77}$ by an -alkylene- or —Y-alkylene-group;

$R_{76}$ is hydrogen, $R_{67}$, monofluoroalkyl, monofluoroalkenyl, aryl-$R_{66}$—, heteroaryl-$R_{66}$—, hydroxyalkyl, HO—$R_{66}$—, $R_{67}$—Y—$R_{66}$—, HS—$R_{66}$—, —C(O)R', —CO$_2$R', or —C(O)N(R')$_2$; or $R_{76}$ may be linked with either $R_{25}$ or $R_{27}$ by an -alkylene- or —Y-alkylene-group;

$R_{82}$ is R', $R_{67}$—Y—$R_{66}$—, $R_{67}$—S(O)—, $R_{67}$—S(O)$_2$—, —SO$_3$R', —S(O)$_2$N(R')$_2$, or D-glucuronidate;

Y is O, —NR'—, —S(O)$_n$—, —C(O)—, —OC(O)—, —C(O)O—, -NR'C(O)—, or —C(O)NR'—;

n is 0, 1, or 2;

q is 72, 73, 76, 77, 78, 79, 82, 83, or 84;

or pharmaceutically acceptable salts thereof.

Preferred dihydrophenanthridinesulfonamides compounds useful in the invention include those of the Groups A-F detailed below.

Group A compounds are those of formula (XII), where the remaining substituents are as defined above.

Group B compounds include those of group A where $R_{32'}$ is hydrogen and the remaining substituents are as defined above.

The compounds of group C include those of group B in which:

$R_{71}, R_{72}, R_{73}, R_{74}, R_{77}, R_{78}, R_{79}, R_{80}, R_{81}, R_{83}, R_{84}$, and $R_{85}$ are each, independently, hydrogen, $R_{67}$, aryl-$R_{66}$—$R_{67}$—Y—$R_{66}$—, hydroxyalkyl, HO—$R_{66}$—, halogen, —OR', —COR', or —CO$_2$R';

$R_{75}$ and $R_{76}$ are each, independently, hydrogen or $R_{67}$;

$R_{66}$ is -alkylene-;

$R_{67}$ is alkyl, aryl, heteroaryl, or perfluoroalkyl;

R' is hydrogen or alkyl; and where the remaining substituents are as defined above.

Group D compounds include those in which the compound is of formula (I) and the remaining substituents are as defined above.

The compounds of group E include the compounds of group D where $R_{63}$ is hydrogen and the remaining substituents are as defined above.

Group F compounds include those of group E in which:
$R_{51}$, $R_{52}$, $R_{53}$, $R_{54}$, $R_{57}$, $R_{58}$, $R_{59}$, $R_{60}$, $R_{61}$, $R_{62}$, $R_{64}$, and $R_{65}$ are each, independently, hydrogen, $R_{67}$, aryl-$R_{66}$—, $R_{67}$—X—$R_{66}$—, hydroxyalkyl, HO—$R_{66}$—, halogen, —OR', —COR', or —CO$_2$R';
$R_{55}$, and $R_{56}$, are each, independently, hydrogen or $R_{67}$;
$R_{66}$ is -alkylene-;
$R_{67}$ is alkyl, aryl, heteroaryl, or perfluoroalkyl;
R' is hydrogen or alkyl;
where the remaining substituents are as defined above.

Yet other compounds useful in the invention are of the formula:

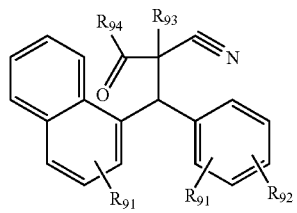

XIII wherein
$R_{91}$ and $R_{92}$ are each independently hydrogen, halo, alkyl, alkoxy, nitro, cyano, thioalkyl, CF$_3$, OCF$_3$, or hydroxy;
$R_{93}$ is H, alkyl, allyl, benzyl, alkenyl, cycloalkyl methyl, or heteroaryl methyl;
$R_{94}$ is NR$_{95}$R$_{96}$, morpholinyl, thiomorpholinyl, t-butylamino,

where z is an integer from 2 to 7

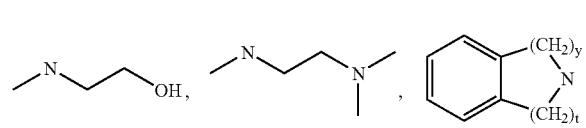

where y is an integer from 1 to 3, and t is 0 or 1,

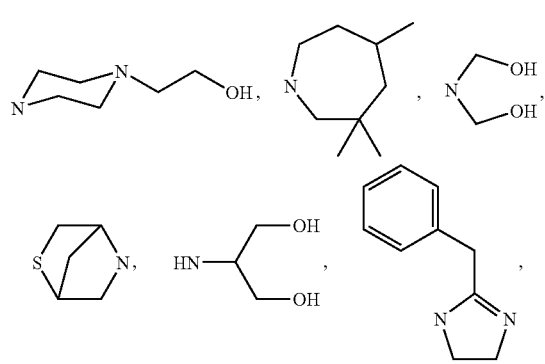

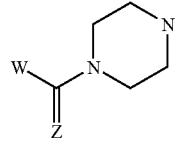

where Z is O or S; and
W is O-aryl, O-heteroaryl, NH-aryl, or NH-heteroaryl;
4-benzylpiperazinyl, 4-heteroarylmethyl piperazinyl, 4-arylmethyl piperazinyl, heteroarylpiperazine, arylpiperazine, heteroaryl tetrahydropyridine, aryl tetrahydropyridine, heteroarylpiperidine, arylpiperidine, or OR$_{96}$;

$R_{95}$ and $R_{96}$ are each, independently, alkyl, heteroaryl methyl, aryl methyl, or cycloalkyl;

and pharmaceutically acceptable salts, hydrates and solvates thereof.

In certain embodiments,
$R_{91}$ and $R_{92}$ are each independently hydrogen, halo, alkyl of 1 to 6 carbon atoms, alkoxy of 1 to 6 carbon atoms, nitro, cyano, thioalkyl, CF$_3$, OCF$_3$, or hydroxy;
$R_{93}$ is H, alkyl of 1 to 6 carbon atoms, allyl, benzyl, alkenyl of 2 to 7 carbon atoms, cycloalkyl methyl, or heteroaryl methyl;
$R_{94}$ is NR$_{95}$R$_{96}$, morpholinyl, thiomorpholinyl, t-butylamino,

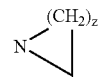

where z is an integer from 2 to 7

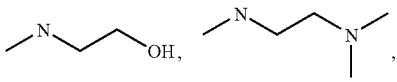

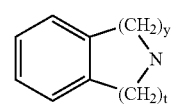

where y is an integer from 1 to 3, and t is 0 or 1,

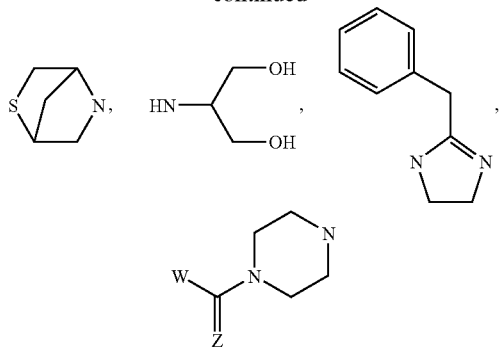

where Z is O or S; and

W is O-aryl, O-heteroaryl, NH-aryl, or NH-heteroaryl;

4-benzylpiperazinyl, 4-heteroarylmethyl piperazinyl, 4-arylmethyl piperazinyl, heteroarylpiperazine, arylpiperazine, heteroaryl tetrahydropyridine, aryl tetrahydropyridine, heteroarylpiperidine, arylpiperidine, or $OR_{96}$; and $R_{95}$ and $R_{96}$ are each, independently, alkyl of 1 to 6 carbon atoms, heteroaryl methyl, aryl methyl, or cycloalkyl of 3 to 8 carbon atoms.

Another class of cyanopropanoic acid derivatives is described as wherein

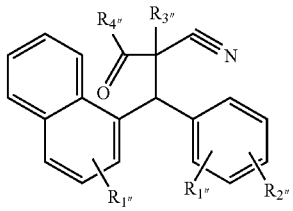

$R_{91}$ and $R_{92}$ are each independently hydrogen, halo, alkyl, alkoxy, nitro, cyano, thioalkyl, $CF_3$, $OCF_3$, or hydroxy;

$R_{93}$ is H, alkyl, allyl, benzyl, or alkenyl, cycloalkyl methyl, or heteroaryl methyl;

$R_{94}$ is $NR_{95}R_{96}$, t-butylamino,

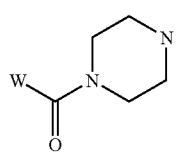

where W is O-heteroaryl, O-aryl, NH-aryl, or NH-heteroaryl, 4-benzyl piperazinyl, 4-heteroarylmethyl piperazinyl, 4-arylmethyl piperazinyl, heteroarylpiperazine, heteroarylpiperazine, heteroaryl tetrahydropyridine, aryl tetrahydropyridine, heteroarylpiperidine, arylpiperidine, $OR_{96;}$ and $R_{95}$ and $R_{96}$ are each independently alkyl, benzyl, alkylene, heteroaryl methyl, aryl methyl, or cycloalkyl.

Another preferred class of cyanopropanoic acid derivatives is described as

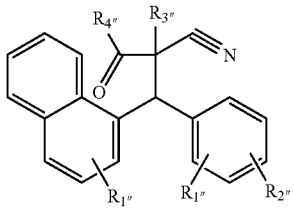

$R_{91}$ and $R_{92}$ are independently hydrogen, halo, alkyl, alkoxy, $CF_3$, $OCF_3$, or hydroxy;

$R_{93}$ is H, alkyl, allyl, benzyl, alkenyl, or aryl methyl, or heteroaryl methyl;

$R_{94}$ is $NR_{95}R_{96}$,

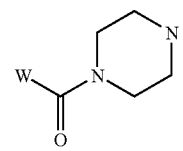

where W is O-aryl, 4-benzyl piperazinyl, 4-heteroarylmethyl piperazinyl, 4-arylmethyl piperazinyl, heteroarylpiperazine, arylpiperazine, heteroaryl tetrahydropyridine, aryl tetrahydropyridine, heteroarylpiperidine, arylpiperidine, or $OR_{96}$; and $R_{95}$ and $R_{96}$ are each independently alkyl, benzyl, heteroaryl methyl, aryl methyl or cycloalkyl.

DEFINITIONS

The term "alkyl", employed alone, is defined herein as, unless otherwise stated, either a $(C_1-C_{20})$ straight chain or $(C_3-C_{20})$ branched-chain monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like. It is preferred that straight chain alkyl moieties have 1-6 carbon atoms, and branched alkyl moieties have 3-8 carbon atoms.

The term "alkenyl", employed alone, is defined herein as, unless otherwise stated, either a $(C_2-C_{20})$ straight chain or $(C_3-C_{20})$ branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like. It is preferred that straight chain alkenyl moieties have 2-7 carbon atoms, and branched alkenyl moieties have 3-8 carbon atoms.

The term "alkynyl", employed alone, is defined herein as, unless otherwise stated, either a $(C_2-C_{20})$ straight chain or $(C_3-C_{20})$ branched-chain monovalent hydrocarbon moiety containing at least one triple bond. Examples of alkynyl moieties include, but are not limited to, chemical groups such as ethynyl, 1-propynyl, 1-(2-propynyl), 3-butynyl, and higher homologs, isomers, and the like. It is preferred that straight chain alkynyl moieties have 2-7 carbon atoms, and branched alkynyl moieties have 3-8 carbon atoms.

The term "alkylene", employed alone or in combination with other terms, is defined herein as, unless otherwise stated, either a ($C_1$-$C_{20}$) straight chain or ($C_2$-$C_{20}$) branched-chain bivalent hydrocarbon moiety derived from an alkane; or a ($C_2$-$C_{20}$) straight chain or branched-chain bivalent hydrocarbon moiety derived from an alkene. Such hydrocarbon alkylene moieties may be fully saturated, or mono or polyunsaturated, and may exist in the E or Z configurations. The compounds of this invention are meant to include all possible E and Z configurations. Examples of saturated and unsaturated hydrocarbon alkylene moieties include, but are not limited to, bivalent chemical groups such as —$CH_2$—, —$CH_2CH_2$—, —$CH_2CH_2CH_2$—, —$CH_2CH_2CH_2CH_2$—, —CH=CH—, —CH=CHCH=CH—, vinylidene, and higher homologs, isomers, and the like. Preferred alkylene chains have 2-7 carbon atoms.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3-10 carbon atoms, wherein the carbon atoms are located inside or outside of the ring system. In some embodiments, the ring comprises 3-8 carbon atoms. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The term "cycloalkenyl", employed alone or in combination with other terms, is defined herein as, unless otherwise stated, a monocyclic, bicyclic, tricyclic, fused, bridged, or spiro monovalent unsaturated hydrocarbon moiety of 3-10 carbon atoms containing at least one double bond, wherein the carbon atoms are located inside or outside of the ring system. In some embodiments, the ring has 4-8 carbon atoms. Any suitable ring position of the cycloalkenyl moiety may be covalently linked to the defined chemical structure. Examples of cycloalkenyl moieties include, but are not limited to, chemical groups such as cyclopropenyl, cyclopropenylmethyl cyclobutenyl, cyclopentenyl, cyclohexenyl, cyclohexenylmethyl, cyclohexenylethyl, cycloheptenyl, norbornenyl, and homologs, isomers, and the like.

The term "cycloalkylene", employed alone, is defined herein as, unless otherwise stated, a bivalent moiety of 3-10 carbon atoms derived from a monocyclic, bicyclic, tricyclic, fused, bridged, or spiro hydrocarbon. In some embodiments, the ring has 4-8 carbon atoms. Such hydrocarbon cycloalkylene moieties may be fully saturated, or mono or polyunsaturated, and may exist in the E or Z configurations. The compounds of this invention are meant to include all possible E and Z configurations. Any suitable ring position of the cycloalkylene moiety may be covalently linked to the defined chemical structure. Examples of saturated and unsaturated hydrocarbon cycloalkylene moieties include, but are not limited to, bivalent chemical groups such as cyclopropylene, cyclopentylene, cyclohexylene, cyclohexenylene, trans-decahydronaphthalenylene, spiro[3.3]heptenylene, and higher homologs, isomers, and the like.

The terms "halo" or "halogen", employed alone or in combination with other terms, is defined herein as, unless otherwise stated, a fluorine, chlorine, bromine, or iodine atom.

The term "monofluoroalkyl", employed alone, is defined herein as, unless otherwise stated, either a ($C_1$-$C_{10}$) straight chain or ($C_3$-$C_{10}$) branched-chain monovalent saturated hydrocarbon moiety containing only one fluorine atom. Examples of monofluoroalkyl moieties include, but are not limited to, chemical groups such as —$CH_2F$, —$CH_2CH_2F$, —$CH(CH_3)CH_2CH_2F$, and higher homologs, isomers, and the like. Preferred chain lengths are from 1-6 carbon atoms for straight chains and from 3-8 carbon atoms for branched chains.

The term "monofluoroalkenyl", employed alone, is defined herein as, unless otherwise stated, either a ($C_2$-$C_{10}$) straight chain or ($C_3$-$C_{10}$) branched-chain monovalent unsaturated hydrocarbon moiety, containing only one fluorine atom and at least one double bond. Examples of monofluoroalkenyl moieties include, but are not limited to, chemical groups such as —CH=$CH_2F$, —$CH_2$CH=$CH_2F$, —CH=CH$CH_2F$, —C($CH_3$)=CHF and higher homologs, isomers, and the like. Preferred chain lengths are from 2-7 carbon atoms for straight chains and from 3-8 carbon atoms for branched chains.

The term "perfluoroalkyl", employed alone or in combination with other terms, is defined herein as, unless otherwise stated, either a ($C_1$-$C_{10}$) straight chain or ($C_3$-$C_{10}$) branched-chain monovalent saturated hydrocarbon moiety containing two or more fluorine atoms. Examples of perfluoroalkyl moieties include, but are not limited to, chemical groups such as trifluoromethyl, —$CH_2CF_3$, —$CF_2CF_3$, and —$CH(CF_3)_2$, and homologs, isomers, and the like. Preferred chain lengths are from 1-7 carbon atoms for straight chains and from 3-8 carbon atoms for branched chains.

The term "aryl", employed alone or in combination with other terms, is defined herein as, unless otherwise stated, an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl. anthryl. phenanthryl, fluorenyl, indanyl, biphenylenyl, acenaphthenyl, acenaphthylenyl, and the like. It is preferred that the aryl moiety contain 6-14 carbon atoms.

The term "arylalkyl", employed alone or in combination with other terms, is defined herein as, unless otherwise stated, an aryl group, as herein before defined, suitably substituted on any open ring position with an alkyl moiety wherein the alkyl chain is either a ($C_1$-$C_6$) straight or ($C_2$-$C_7$) branched-chain saturated hydrocarbon moiety. In certain embodiments, arylalkyl groups have 7 to 26 carbon atoms. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "heterocyclic ring system" is defined as being 4 to 14 carbon atoms. he rings may contain from one to four hetero atoms selected from nitrogen (N), oxygen (O), or sulfur (S), wherein the nitrogen or sulfur atom(s) are optionally oxidized, or the nitrogen atom(s) are optionally substituted or quarternized. Any suitable ring position of the heteroaryl moiety may be covalently linked to the defined chemical structure. The ring may be saturated, unsaturated, or partially unsaturated. Heterocyclic rings may comprise a single ring or a multiple ring system comprising up to three rings.

The term "heteroaryl", employed alone or in combination with other terms, is defined herein as, unless otherwise stated, an aromatic heterocyclic ring system, which may be a single ring (monocyclic) or multiple rings (bicyclic, up to three rings) fused together or linked covalently. The rings may contain from one to four hetero atoms selected from nitrogen (N), oxygen (O), or sulfur (S), wherein the nitrogen or sulfur atom(s) are optionally oxidized, or the nitrogen atom(s) are optionally substituted or quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole, 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like.

The term "heteroarylalkyl", employed alone or in combination with other terms, is defined herein as, unless otherwise stated, a heteroaryl group, as herein before defined, suitably substituted on any open ring position with an alkyl moiety, wherein the alkyl chain is either a $(C_1-C_6)$ straight or $(C_2-C_7)$ branched-chain saturated hydrocarbon moiety. Examples of heteroarylalkyl moieties include, but are not limited to, chemical groups such as furanylmethyl, thienylethyl, indolylmethyl, and the like.

Heteroaryl chemical groups, as herein before defined, also include saturated or partially saturated heterocyclic rings. Examples of saturated or partially saturated heteroaryl moieties include, but are not limited to, chemical groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

The term "acyl", employed alone or in combination with other terms, is defined herein as, unless otherwise stated, either an alkyl, arylalkyl, heteroarylalkyl, $(C_2-C_{10})$ straight chain, or $(C_4-C_{11})$ branched-chain monovalent hydrocarbon moiety; wherein the carbon atom, covalently linked to the defined chemical structure, is oxidized to the carbonyl oxidation state. Such hydrocarbon moieties may be mono or polyunsaturated, and may exist in the E or Z configurations. The compounds of this invention are meant to include all possible E and Z configurations. Examples of acyl moieties include, but are not limited to, chemical groups such as acetyl, propionyl, butyryl, 3,3-dimethylbutyryl, trifluoroacetyl, pivaloyl, hexanoyl, hexenoyl, decanoyl, benzoyl, nicotinyl, isonicotinyl, and homologs, isomers, and the like.

The term "hydroxyalkyl", employed alone or in combination with other terms, is defined herein as, unless otherwise stated, a $(C_1-C_{10})$ straight chain hydrocarbon, terminally substituted with a hydroxyl group. Examples of hydroxyalkyl moieties include chemical groups such as —CH$_2$OH, —CH$_2$CH$_2$OH, —CH$_2$CH$_2$CH$_2$OH, and higher homologs.

The term "alkoxy", employed alone or in combination with other terms, is defined herein as, unless otherwise stated, either a $(C_1-C_{10})$ straight chain or $(C_3-C_{10})$ branched-chain hydrocarbon covalently bonded to an oxygen atom. Examples of alkoxy moieties include, but are not limited to, chemical groups such as methoxy, ethoxy, isopropoxy, sec-butoxy, tert-butoxy, decanoxy, and homologs, isomers, and the like. In certain embodiments, the alkoxy group has 1-6 carbon atoms.

The terms "aryloxy" or "heteroaryloxy", employed alone or in combination with other terms, or unless otherwise stated, are aryl or heteroaryl groups, as herein before defined, which are further covalently bonded to an oxygen atom. Examples of aryloxy, or heteroaryloxy moieties include, but are not limited to, chemical groups such as C$_6$H$_5$O—, 4-pyridyl-O—, and homologs, isomers, and the like.

The term "carbonyl", employed alone or in combination with other terms, is defined herein as, unless otherwise stated, a bivalent one-carbon moiety further bonded to an oxygen atom with a double bond. An example is

The term "alkoxycarbonyl", employed alone or in combination with other terms, is defined herein as, unless otherwise stated, an alkoxy group, as herein before defined, which is further bonded to a carbonyl group to form an ester moiety. Examples of alkoxycarbonyl moieties include, but are not limited to, chemical groups such as methoxycarbonyl, ethoxycarbonyl, isopropoxycarbonyl, sec-butoxycarbonyl, tert-butoxycarbonyl, decanoxycarbonyl, and homologs, isomers, and the like.

The term "alkylthio", employed alone or in combination with other terms, is defined herein as, unless otherwise stated, either a $(C_1-C_{10})$ straight chain or $(C_3-C_{10})$ branched-chain hydrocarbon moiety covalently bonded to a sulfur atom. Examples of alkylthio moieties include, but are not limited to, chemical groups such as methylthio, ethylthio, isopropylthio, sec-butylthio, tert-butylthio, decanylthio, and homologs, isomers, and the like. It is preferred that straight chain alkylthio moieties have 1-6 carbon atoms, and branched alkylthio moieties have 3-8 carbon atoms.

The terms "arylthio" or "heteroarylthio", employed alone or in combination with other terms, or unless otherwise stated, are aryl or heteroaryl groups, as herein before defined, which are further covalently bonded to a sulfur atom. Examples of arylthio or heteroarylthio moieties include, but are not limited to, chemical groups such as C$_6$H$_5$S—, 4-pyridyl-S—, and homologs, isomers, and the like.

The terms "alkoxyalkyl" or "alkylthioalkyl", employed alone or in combination with other terms, are an alkoxy or alkylthio group, as herein before defined, which is further covalently bonded to an unsubstituted $(C_1-C_{10})$ straight chain or unsubstituted $(C_2-C_{10})$ branched-chain hydrocarbon. Examples of alkoxyalkyl or alkylthioalkyl moieties include, but are not limited to, chemical groups such as methoxymethyl, methylthioethyl, ethylthioethyl, isopropylthiomethyl, sec-butylthioethyl, —CH$_2$CH(CH$_3$)OCH$_2$CH$_3$, and homologs, isomers, and the like. It is preferred that straight chain alkoxyalkyl or alkylthioalkyl moieties have 1-6 carbon atoms, and branched alkoxyalkyl or alkylthioalkyl moieties have 3-8 carbon atoms.

The terms "aryloxyalkyl", "heteroaryloxyalkyl", "arylthioalkyl", or "heteroarylthioalkyl", employed alone or in combination with other terms, or unless otherwise stated, are aryloxy, heteroaryloxy, arylthio, or heteroarylthio groups, as herein before defined, which are further covalently bonded to an unsubstituted (C$_1$-C$_{10}$) straight chain or unsubstituted (C$_2$-C$_{10}$) branched-chain hydrocarbon. Examples of aryloxyalkyl, heteroaryloxyalkyl, arylthioalkyl, or heteroarylthioalkyl moieties include, but are not limited to, chemical groups such as C$_6$H$_5$OCH$_2$—, C$_6$H$_5$OCH(CH$_3$)—, 4-pyridyl-O—CH$_2$CH$_2$—, C$_6$H$_5$SCH$_2$—, C$_6$H$_5$SCH(CH$_3$)—, 4-pyridyl-S—CH$_2$CH$_2$—, and homologs, isomers, and the like. It is preferred that straight chain aryloxyalkyl, heteroaryloxyalkyl, arylthioalkyl, or heteroarylthioalkyl moieties have 1-6 carbon atoms, and branched aryloxyalkyl, heteroaryloxyalkyl, arylthioalkyl, or heteroarylthioalkyl moieties have 3-8 carbon atoms.

The term "alkylamino", employed alone or in combination with other terms, or unless otherwise stated, is a moiety with one alkyl group, wherein the alkyl group is an unsubstituted (C$_1$-C$_6$) straight chain hereunto before defined alkyl group or an unsubstituted (C$_3$-C$_8$) hereunto before defined cycloalkyl group. Examples of alkylamino moieties include, but are not limited to, chemical groups such as —NH(CH$_3$), —NH(CH$_2$CH$_3$), —NH-cyclopentyl, and homologs, and the like.

The term "dialkylamino", employed alone or in combination with other terms, or unless otherwise stated, is a moiety with two independent alkyl groups, wherein the alkyl groups are unsubstituted (C$_1$-C$_6$) straight chain hereunto before defined alkyl groups or unsubstituted (C$_3$-C$_8$) hereunto before defined cycloalkyl groups. Two groups may be linked to form an unsubstituted (C$_1$-C$_6$)-alkylene-group. Examples of dialkylamino moieties include, but are not limited to, chemical groups such as —N(CH$_3$)$_2$, —N(CH$_2$CH$_3$)$_2$, —NCH$_3$(CH$_2$CH$_3$),

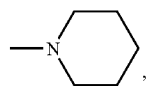

and homologs, and the like.

The term "alkylaminoalkyl" employed alone or in combination with other terms, or unless otherwise stated, is an alkylamino moiety, as herein before defined, which is further covalently bonded to a straight chain alkyl group of 1-6 carbon atoms. Examples of alkylaminoalkyl moieties include, but are not limited to, chemical groups such as —CH$_2$NH(CH$_3$), —CH$_2$CH$_2$NH(CH$_2$CH$_3$), —CH$_2$CH$_2$CH$_2$NH(CH$_2$CH$_3$), and homologs, and the like.

The term "dialkylaminoalkyl" employed alone or in combination with other terms, or unless otherwise stated, is a dialkylamino moiety, as herein before defined, which is further covalently bonded to a straight chain alkyl group of 1-6 carbon atoms. Examples of dialkylaminoalkyl moieties include, but are not limited to, chemical groups such as —CH$_2$N(CH$_3$)$_2$, —CH$_2$CH$_2$N(CH$_2$CH$_3$)$_2$, —CH$_2$CH$_2$CH$_2$NCH$_3$(CH$_2$CH$_3$), and homologs, and the like.

The terms "alkylaminocarbonyl" or "dialkylaminocarbonyl", employed alone, or unless otherwise stated, are alkylamino or dialkylamino moieties, as herein before defined, which are further bonded to a carbonyl group. Examples of alkylaminocarbonyl or dialkylaminocarbonyl moieties include, but are not limited to, chemical groups such as —C(O)NH(CH$_3$), —C(O)N(CH$_2$CH$_3$)$_2$, —C(O)NCH$_3$(CH$_2$CH$_3$), and homologs, and the like.

Each of the above terms (e.g., alkyl, aryl, heteroaryl) includes unsubstituted, monosubstituted, and polysubstituted forms of the indicated radical or moiety. Representative substituents for each type of moiety are provided below.

Substituents for alkyl, alkenyl, alkynyl, cycloalkyl, cycloalkenyl, alkylene, cycloalkylene, the alkyl portion of arylalkyl and heteroarylalkyl, saturated or partially saturated heterocyclic rings, and acyl or carbonyl moieties can be, employed alone or in combination with other terms, —R', OR', =O, =NR', =N—OR', —NR'R", —SR', halo, trifluoromethyl, trifluoromethoxy, —OC(O)R', —CO$_2$R', —C(O)NR'R", —OC(O)NR'R", —NR"C(O)R', —NR"CO$_2$R', —NR'C(O)NR'R", —NH—C(NH$_2$)=NH, —NR'C(NH$_2$)=NH, —NH—C(NH$_2$)=NR', —S(O)R', —S(O)$_2$R', —S(O)$_2$NR'R", cyano, and nitro; wherein, R' or R" are each, independently, hydrogen, unsubstituted (C$_1$-C$_6$)alkyl, unsubstituted (C$_3$-C$_7$)cycloalkyl, aryl, aryl-(C$_1$-C$_3$)alkyl, aryloxy-(C$_1$-C$_3$)alkyl, arylthio-(C$_1$-C$_3$)alkyl, heteroaryl, heteroaryl-(C$_1$-C$_3$)alkyl, heteroaryloxy-(C$_1$-C$_3$)alkyl, or heteroarylthio-(C$_1$-C$_3$)alkyl groups; or if optionally taken together may be linked as an -alkylene-group to form a ring.

The aryl or heteroaryl moieties, employed alone or in combination with other terms, may be optionally mono-, di- or tri-substituted with substituents selected from the group consisting of —R', —OR', —SR', —C(O)R', —CO$_2$R', -alkoxyalkyl, alkoxyalkyloxy, cyano, halogen, nitro, trifluoromethyl, trifluoromethoxy, —NR'R", alkylaminoalkyl, dialkylaminoalkyl, hydroxyalkyl, —S(O)R', —S(O)$_2$R', —SO$_3$R', —S(O)$_2$NR'R", —CO$_2$R', —C(O)NR'R", —OC(O)NR'R", —NR"C(O)R', —NR"CO$_2$R', —NR'C(O)NR'R", —NH—C(NH$_2$)=NH, —NR'C(NH$_2$)=NH, —NH—C(NH$_2$)=NR', —S(O)R', and —S(O)$_2$R'; wherein, R' or R" are each, independently, hydrogen, (C$_1$-C$_6$)alkyl, (C$_3$-C$_7$)cycloalkyl, aryl, aryl-(C$_1$-C$_3$)alkyl, aryloxy-(C$_1$-C$_3$) alkyl, arylthio-(C$_1$-C$_3$)alkyl, heteroaryl, heteroaryl-(C$_1$-C$_3$) alkyl, heteroaryloxy-(C$_1$-C$_3$)alkyl, or heteroarylthio-(C$_1$-C$_3$) alkyl groups; or if optionally taken together may be linked as an -alkylene-group to form a ring.

As used herein, the term "a substantial absence of creatine kinase stimulation" means the compound has an IC$_{50}$ value greater than 1 µmol with an efficacy of less than 30% compared to 17-β-estradiol.

The phrase "a substantial absence of uterotropic activity" means that no statistically significant uterine wet weight gain is observed.

A pro-drug is defined as a compound which is convertible by in vivo enzymatic or non-enzymatic metabolism (e.g. hydrolysis) to a compound of the invention.

The compounds of the present invention may contain an asymmetric atom, and some of the compounds may contain one or more asymmetric atoms or centers, which may thus give rise to optical isomers (enantiomers) and diastereomers. While shown without respect to the stereochemistry in Formula (I) or (II), the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers may be obtained in pure form by standard procedures known to those skilled in the art, and include, but are not limited to, diasteromeric salt formation, kinetic resolution, and asymmetric synthesis. It is also understood that this invention encompasses all possible regioisomers, and mixtures thereof, which may be obtained in pure form by standard separation procedures known to those skilled in the art, and include, but are not limited to, column chromatography, thin-layer chromatography, and high-performance liquid chromatography.

The compounds of the present invention may contain isotopes of atoms for diagnostic, therapeutic, or metabolic purposes. Such isotopes may or may not be radioactive.

The compounds of this invention include racemates, enantiomers, geometric isomers, or pro-drugs of the compounds described herein.

As used herein, the term "pharmaceutically acceptable" refers to a carrier medium which does not interfere with the effectiveness of the biological activity of the active ingredient(s) and which is not toxic to the host to which it is administered.

Pharmaceutically acceptable salts of the compounds of the invention with an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, maleic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

As used in accordance with this invention, the term "providing," with respect to providing a compound or substance covered by this invention, means either directly administering such a compound or substance, or administering a pro-drug, derivative, or analog which will form the effective amount of the compound or substance within the body. This invention also covers providing the compounds of this invention to treat the disease states disclosed herein that the compounds are useful for treating.

As used herein, the terms "therapeutically effective amount" and "therapeutically effective dose" as applied to the active ingredient refers to the amount of the component in the composition or administered to the host that results in an increase in the therapeutic index of the host. The "therapeutic index" can be defined for purposes herein in terms of efficacy, i.e., extent of reduction or inhibition of inflammation. Suitable doses of the active ingredient can be determined using well-known methods, a variety of which are known and readily available in the pharmaceutical sciences, including, for example, measurement of markers associated with the disorder, the biological effects of TNF-$\alpha$, and decreased symptomatology.

It is understood that the effective dosage of the active compounds of this invention may vary depending upon the particular compound utilized, the mode of administration, the condition, and severity thereof, of the condition being treated, as well as the various physical factors related to the individual being treated. It is projected that compounds of this invention will be administered at an oral daily dosage of from about 0.05 mg to about 30 mg per kilogram of body weight, preferably administered in divided doses two to six times per day, or in a sustained release form. For most large mammals, the total daily dosage is from about 3.5 mg to about 2100 mg, preferably from about 3.5 to about 5 mg. In the case of a 70 kg human adult, the total daily dose will generally be from about 3.5 mg to about 2100 mg and may be adjusted to provide the optimal therapeutic result.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, sweetening agents, lubricants, solubilizers, suspending agents, fillers, glidants, compression aids, binders, or tablet-disintegrating agents; it can also be an encapsulating material. In powders, the carrier is a finely divided solid which is in admixture with the finely divided active ingredient.

Solid dosage unit forms or compositions such as tablets, troches, pills, capsules, powders, and the like, may contain a solid carrier binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose, or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both.

Liquid carriers are used in preparing liquid dosage forms such as solutions, suspensions, dispersions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution); alcohols, including monohydric alcohols such as ethanol and polyhydric alcohols such as glycols and their derivatives; lethicins, and oils such as fractionated coconut oil and arachis oil. For parenteral administration, the liquid carrier can also be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant.

A liquid pharmaceutical composition such as a syrup or elixir may contain, in addition to one or more liquid carriers and the active ingredients, a sweetening agent such as sucrose, preservatives such as methyl and propyl parabens, a pharmaceutically acceptable dye or coloring agent, or a flavoring agent such as cherry or orange flavoring.

Liquid pharmaceutical compositions which are sterile solutions or suspensions can be administered intraocularly or parenterally, for example, by intramuscular, intraperitoneal or subcutaneous injection. Sterile solutions can also be administered intravenously. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under the conditions of manufacture and storage and must be preserved against the contaminating action of microorganisms such as bacteria and fungi. The carrier can be a solvent or dispersion medium containing a liquid carrier, for example, water, ethanol, polyol (e.g. glycerol, propylene glycol and liquid polyethylene glycol), suitable mixtures thereof, and vegetable oils. The liquid carrier may be suitably mixed with a surfactant such as hydroxypropylcellulose.

The compounds of the present invention may also be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may be administered topically, or also transdermally through the use of a transdermal patch containing the active compound and a carrier that is inert to the active compound, which is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

EXAMPLES

The following describes the preparation of representative compounds of this invention. Compounds described as homogeneous were determined to be 98% or greater a single peak (exclusive of enantiomers) by analytical reverse phase chromatographic analysis with 254 nM UV detection. Melting points are reported as uncorrected in degrees centigrade. The infrared data is reported as wave numbers at maximum absorption, $v_{max}$ in reciprocal centimeters, $cm^{-1}$. Mass spectral data is reported as the mass-to-charge ratio, m/z; and for high resolution mass spectral data, the calculated and experimentally found masses, $[M+H]^+$, for the neutral formulae M are reported. Nuclear magnetic resonance data is reported as δ in parts per million (ppm) downfield from the standard, tetramethylsilane; along with the solvent, nucleus, and field strength parameters. The spin-spin homonuclear coupling constants are reported as J values in hertz; and the multiplicities are reported as a: s, singlet; d, doublet; t, triplet; q, quartet; quintet; or br, broadened. Italicized elements or groups are those responsible for the chemical shifts. The yields given below are for informational purposes and may vary according to experimental conditions or individual techniques.

Representative compounds of this invention were evaluated in the following standard pharmacological test procedures which demonstrated the anti-inflammatory activity for the compounds of this invention. The test procedures used and the results obtained are briefly described below.

Example 1

4-(1,7-disubstituted-1H-indazol-3-yl)phenols

Step A: A solution of (2-fluoro-3-substituted-phenyl)(4-methoxy-2-substituted-phenyl)methanone (1 equivalent), hydrazine hydrate (10 eq.) and DMAP (1 eq.) in pyridine was heated at 100° C. for 24-48 hrs. The cooled reaction mixture was partitioned with EtOAc and 1 N HCl. The organic phase was washed with brine and dried ($Na_2SO_4$). The resulting residue was purified by flash chromatography to give the intermediate 3-(4-methoxyphenyl)-7-substituted-1-1H-indazole.

Step B: A solution of the intermediate 3-(4-methoxyphenyl)-7-substituted-1-1H-indazole (1 eq.) in DMF was added in one portion sodium hydride (1 eq., 60% in oil). After the gas evolution ceased, the alkyl halide was added and the reaction was stirred at ambient to 50° C. overnight. The cool reaction mixture was partitioned with EtOAc and 1 N HCl. The organic phase was washed with brine and dried ($Na_2SO_4$). The resulting residue was purified by flash chromatography or by HPLC chromatography through silica gel columns 150×12 mm (Biotage) at 10 mL/min with methyl-t-butyl ether/hexane (gradient elution 1:9 to 1:1) to give the intermediates 3-(4-methoxyphenyl)-7-substituted-1-substituted-1H-indazole and 3-(4-methoxyphenyl)-7-substituted-2-substituted-2H-indazole.

Step C: A solution of 3-(4-methoxyphenyl)-7-substituted-(1 or 2-substituted)-(1H or 2H)-indazole (1 eq.) in $CH_2Cl_2$ containing excess equivalents of cyclohexene at −78° C. was treated with boron tribromide (4 eq.) and slowly allowed to warm to ambient temperature. The reaction was quenched by dropwise edition of $CH_3OH$ to the cooled reaction. The solvent was removed in vacuo and the residue partitioned with EtOAc and 1 N HCl. The organic phase was washed with brine and dried ($Na_2SO_4$). Removal of the solvent in vacuo afforded the crude product. Pure product was obtained by crystallization or flash chromatography through water deactivated silica gel. Note: HPLC retention times were obtained using the following conditions:

| Column: | Keystone Aquasil C18 (50 × 2 mm, 5 u), |
|---|---|
| Solvent System: | A: 95% 10 mM NH4OAc/5% acetonitrile, |
| | B: 95% acetonitrile 5% 10 mM NH4OAc, |
| Gradient | 0% B to 100% B over 0-15 minutes, |
| Flow | 0.8 mL/min |
| Detection: | UV. various wavelengths |

Example 2

4-[1-allyl-7-(trifluoromethyl)-1H-indazol-3-yl]benzene-1,3-diol

Step 1: 1-allyl-3-(2,4-dimethoxyphenyl)-7-(trifluoromethyl)-1H-indazole

Prepared according to Example 1, step B from 3-(2,4-methoxyphenyl)-7-trifluoromethyl-1H-indazole 0.52 g, 1.6 mmol), sodium hydride (60% in oil, 0.065 g, 1.6 mmol) and allyl bromide (0.138 mL, 1.6 mmol) to give the title compound (0.26 g) as a white solid.

$^1$H NMR (DMSO-d$_6$): δ 3.73 (s, 3H), 3.80 (s, 3H), 4.85 (dd, 1H, J=1.5 and 14.65), 5.1 (m, 3H), 5.97-6.05 (m, 1H), 6.39 (dd, 1H, J=2.32 and 6.14), 6.64 (s, 1H), 7.25 (t, 1H), 7.35 (d, 1H), 7.85-7.87 (m, 2H),). MS (ESI) m/z 363 [M+H]+.

Step 2: 4-[1-allyl-7-(trifluoromethyl)-1H-indazol-3-yl]benzene-1,3-diol

Prepared according to Example 1, step C from 1-allyl-3-(2,4-dimethoxyphenyl)-7-(trifluoromethyl)-1H-indazole (0.065 g, 0.18 mmol), boron tribromide (0.136 mL, 1.4 mmol) and 1.0 mL of cyclohexene to give the product (0.066 g) as a white solid, mp 114-115° C.;

$^1$H NMR (DMSO-d$_6$): δ 4.87 (dd, 1H, J=1.37 and 17.10 Hz), 5.31-5.08 (m, 3H), 6.01-6.08 (m, H), 6.39 (dd, 1H, J=2.44 and 8.40 Hz), 6.46 (s, 1H), 7.30 (t, 1H), 3.78 (d, 1H), 7.85-7.87 (m, 1H), 8.14-8.19 (m, 1H), 9.59 (broad s, 1H), 9.82 (broad s, 1H) MS (ESI) m/z 335 [M+H]+. Anal. calcd for $C_{17}H_{13}F_3N_2O_2$: C,61.08; H,3.92; N,8.38. Found: C,61.02; H,3.76; N,8.28.

Example 3

4-[(8-Fluoro-6-methylphenanthridin-5(6H)-yl)sulfonyl]phenol

Step 1: N-(4'-Fluorobiphenyl-2-yl)acetamide

A stirred solution of 2-iodoaniline (32.6 g, 149 mmol) and 4-fluorophenylboronic acid (20.8 g, 149 mmol) in tetrahydrofuran (1.5 L) was treated under nitrogen with [1,1'-bis(diphenylphosphino)ferrocene]dichloropalladium (II) complex with dichloromethane (2.20 g, 2.69 mmol) and a 5 N sodium hydroxide solution (60 mL). The reaction mixture was heated at reflux for twelve hours, cooled to room temperature, and the solvent removed in vacuo. The residue was dissolved in ethyl acetate (250 mL) and extracted with a saturated, aqueous, sodium chloride solution (100 mL). The aqueous phase was further extracted with ethyl acetate (2×50 mL). The combined organic phase was dried over anhydrous magnesium sulfate, filtered, and concentrated in vacuo to a brown oil. The brown oil was filtered through a short column of silica gel, and eluted with a mixture of ethyl acetate-hexane (1:4). After evaporation of the solvent in vacuo, a solution of the crude 4'-fluoro-biphenyl-2-ylamine in dichloromethane (75 mL) was treated with pyridine (27.7 mL, 343 mmol), acetic anhydride (15.5 mL, 164 mmol), and 4-(N,N-dimethylamino)pyridine (0.55 g, 4.5 mmol). After stirring for twelve hours at room temperature, the reaction was quenched with a saturated, aqueous, ammonium. chloride solution (250 mL). The separated aqueous phase was extracted with dichloromethane (3×75 mL), and the combined organic phase washed sequentially with a 0.1 N hydrochloric acid solution (2×50 mL), and a saturated, aqueous, sodium bicarbonate solution (50 mL). The organic phase was dried over anhydrous sodium sulfate, filtered and concentrated in vacuo to a second brown oil. After toluene was added and removed in vacuo (3×), the resulting brown solid was crystallized from ethyl acetate-hexane to yield a first crop of the desired product (19.0 g). The mother liquor was concentrated and purified by flash column chromatography on silica gel, eluting with ethyl acetate-hexane (1:4), to obtain a second crop (5.0 g). The combined crops afforded the title compound as a homogeneous, colorless, crystalline, solid (24.0 g, 70%). m.p. 123-124° C.; MS [(+ESI), m/z]: 230 [M+H]+;

$^1$H NMR (500 MHz, DMSO-d$_6$) δ: 9.24 (s, 1H), 7.44-7.23 (m, 8H), 1.87 (s, 3H); Anal. calcd for $C_{14}H_{12}FNO$: C, 73.35; H, 5.28; N, 6.11. Found: C, 73.09; H, 5.20; N, 5.89.

Step 2: 8-Fluoro-6-methylphenanthridine

The N-(4'-fluorobiphenyl-2-yl)acetamide (18.5 g, 80.7 mmol) was mixed with polyphosphoric acid (250 g) and heated at 120° C. with vigorous stirring for 48 hours. The hot reaction mixture was poured onto ice and stirred vigorously until homogeneous. Ammonium hydroxide (28-30%, aqueous) was added until the pH was greater than eight. A white precipitate was filtered, dissolved in ethyl acetate (250 mL), and re-filtered. The combined filtrate was washed with a saturated, aqueous, sodium chloride solution, dried over anhydrous sodium sulfate, filtered, and evaporated in vacuo to a brown solid. The brown solid was purified by crystallization from a mixture of ethyl acetate-hexane to yield the title compound as a white, crystalline solid (15.9 g, 94%), m.p. 92-93° C.; MS [(+ESI), m/z]: 212 [M+H]+;

$^1$H NMR (500 MHz, CDCl$_3$) δ: 8.63 (dd, J=9.0, 5.4 Hz, 1H), 8.49 (dd, J=8.2, 1.0 Hz, 1H), 8.10 (dd, J=8.1, 1.1 Hz, 1H), 7.84 (dd, J=9.6, 2.6 Hz, 1H), 7.71 (m, 1H), 7.65-7.57 (m, 2H), 3.01 (s, 3H);

$^1$H NMR (400 MHz, DMSO-d$_6$) δ: 8.89 (dd, J=9.1, 5.6 Hz, 1H), 8.70 (dd, J=8.1, 1.3 Hz, 1H), 8.05 (dd, J=10.1, 2.5 Hz, 1H), 7.97 (dd, J=8.1, 1.3 Hz, 1H), 7.80 (m, 1H), 7.70 (m, 1H), 7.63 (m, 1H), 3.01 (s, 3H); Anal. calcd for $C_{14}H_{10}FN.0.10 H_2O$: C, 78.93; H, 4.83; N, 6.57. Found: C, 78.90; H, 4.57; N, 6.58.

Step 3: 4-(Chlorosulfonyl)phenyl ethyl carbonate

A solution of sodium 4-hydroxybenzenesulfonate dihydrate (50.0 g, 215 mmol) in 1.25 N aqueous sodium hydroxide (170 mL, 213 mmol) was treated drop-wise with ethyl chloroformate (20.6 mL, 215 mmol). The reaction mixture was stirred for twelve hours at room temperature. After cooling the mixture to 0° C., a white precipitate, which formed under the reaction conditions, was filtered. The solid was dried in vacuo at 70° C. The white solid (40.0 g) was suspended in toluene (350 mL) and treated with N,N-dimethylformamide (6.0 mL) and thionyl chloride (22.0 mL, 298 mmol), and the resulting mixture was heated at 100° C. for twelve hours. After cooling to room temperature, the reaction mixture was filtered through diatomaceous earth. The filtrate was concentrated in vacuo, and the resulting oil solidified upon standing. The solidified oil was dissolved in ethyl acetate-hexane (1:4), filtered through a short column of silica gel, and the solvent removed in vacuo to yield the sulfonyl chloride as a white solid (34.8 g, 61%), m.p. 74-76° C.;

¹H NMR (400 MHz, DMSO-d₆) δ: 7.60 (d, J=8.7 Hz, 2H), 7.14 (d, J=8.8 Hz, 2H), 4.23 (q, J=7.1 Hz, 2H), 1.26 (t, J=7.1 Hz, 3H).

Step 4: Ethyl 4-[(8-fluoro-6-methylphenanthridin-5 (6H)-yl)sulfonyl]phenyl carbonate A stirred solution of 8-fluoro-6-methylphenanthridine (8.00 g, 37.9 mmol) in tetrahydrofuran (152 mL) was treated with freshly crushed sodium borohydride (7.16 g, 189 mmol). Trifluoroacetic acid (11.7 mL, 152 mmol) was added drop-wise at a rate suitable to control gas evolution and exothermic reaction conditions. After the trifluoroacetic acid addition was completed, the heterogeneous reaction mixture was stirred until the reaction returned to room temperature; then was re-heated to reflux for 14 hours. After cooling to room temperature, a saturated, aqueous, sodium bicarbonate solution (250 mL) was slowly added. The mixture was filtered through a plug of glass wool, and extracted with diethyl ether (4×75 mL). The combined organic extract was dried over anhydrous sodium sulfate, filtered, and concentrated in vacuo to afford the dihydrophenanthridine as a light-brown paste. A solution of the crude dihydrophenanthridine in dichloromethane (38 mL) was treated with triethylamine (31.7 mL, 227 mmol) and 4-(chlorosulfonyl) phenyl ethyl carbonate (12.0 g, 45.3 mmol), and stirred at room temperature for 14 hours. The reaction was quenched with a 0.1 N sodium hydroxide solution (150 mL) and extracted with dichloromethane (6×50 mL). The combined organic extract was washed with a 2 N hydrochloric acid solution (2×40 mL), dried over anhydrous sodium sulfate, filtered, and concentrated in vacuo to a viscous, brown oil. The brown oil was triturated with hexane (25 mL) to afford a light-brown solid. The light-brown solid was purified by crystallization from a mixture of ethyl acetate-hexane to yield a first crop of the desired product. The mother liquor was concentrated in vacuo, and purified by filtration through a plug of silica gel, eluting with ethyl acetate-hexane (1:4), to obtain a second crop. The combined crops afforded the title compound as a white, crystalline solid (15.2 g, 91%), m.p. 136-138° C.; MS [(+ESI), m/z]: 442 [M+H]⁺;

¹H NMR (500 MHz, DMSO-d₆) δ: 7.77 (d, J=7.6 Hz, 1H), 7.63 (d, J=7.8 Hz, 1H), 7.48-7.39 (m, 3H), 7.19 (dd, J=9.0, 2.6 Hz, 1H), 7.09 (d, J=8.7 Hz, 2H), 6.98 (d, J=8.7 Hz, 2H), 6.93 (td, J=8.7, 2.6 Hz, 1H), 5.48 (q, J=7.0 Hz, 1H), 4.21 (q, J=7.1 Hz, 2H), 1.25 (t, J=7.1 Hz, 3H), 1.15 (t, J=7.0 Hz, 3H); Anal. calcd for $C_{23}H_{20}FNO_5S$: C, 62.57; H, 4.57; N, 3.17. Found: C, 62.51; H, 4.47; N, 2.96.

Step 5: 4-[(8-Fluoro-6methylphenanthridin-5(6H)-yl)sulfonyl]phenol

A solution of ethyl 4-[(8-fluoro-6-methylphenanthridin-5 (6H)-yl)sulfonyl]phenyl carbonate (0.45 g, 1.02 mmol) in methanol (5.0 mL) was treated with a 1 N sodium hydroxide (5.1 mL) solution, and heated at 75° C. for 14 hours. After cooling to room temperature, the methanol was evaporated in vacuo. The resulting aqueous mixture was acidified with a 1 N hydrochloric acid solution, diluted with a saturated, aqueous, sodium chloride solution (100 mL), and extracted with dichloromethane (5×15 mL). The combined organic phase was dried over anhydrous sodium sulfate, filtered, and concentrated in vacuo to a white solid. The solid was purified by filtration through a short column of silica gel, eluting with ethyl acetate, to yield the title compound as a homogeneous, white, crystalline, solid (0.34 g, 89%), m.p. 188° C.; MS [(-ESI), m/z]: 368 [M-H]⁻;

¹H NMR (500 MHz, DMSO-d₆) δ: 10.24 (br s, 1H), 7.76 (dd, J=7.6 Hz, 1.5, 1H), 7.60 (dd, J=7.8, 1.4 Hz, 1H), 7.52 (dd, J=8.7, 5.0 Hz, 1H), 7.41 (m, 1H), 7.37 (m, 1H), 7.17 (dd, J=9.2, 2.7 Hz, 1H), 6.96 (td, J=8.7, 2.7 Hz, 1H), 6.86 (d, J=8.9 Hz, 2H), 6.38 (d, J=8.9 Hz, 2H), 5.41 (q, J=7.0 Hz, 1H), 1.13 (d, J=7.0 Hz, 3H); Anal. calcd for $C_{20}H_{16}FNO_3S$: C, 65.03; H, 4.37; N, 3.79. Found: C, 64.77; H, 4.31; N, 3.76.

Example 4

(S)-3-[4-(3,5-dimethoxyphenyl)piperazin-1-yl]-2-[(S)-(2-methoxyphenyl)(1-naphthyl)methyl]-2-methyl-3-oxopropanenitrile A solution of (S,S)2-cyano-3-(2-methoxy-phenyl)-2-methyl-3-naphthalen-1-yl-propionic acid (0.45 g, 1.30 mmol) in THF (150 mL) is treated with DMF (2 drops). Oxalyl chloride (0.16 mL, 1.84 mmol) is added dropwise in order to control gas evolution; when the gas evolution stopped the solution is heated to reflux for 5 minutes. The solution is cooled, the THF is evaporated in vacuo and the solid is dissolved in dry toluene (15 mL) and evaporated to a solid. This procedure is repeated twice. The acid chloride is dissolved in dichloromethane (10 mL) this is added to a solution of 1-(3,5-dimethoxy-phenyl)-piperazine (305 mg, 1.36 mmol) and a crystal of DMAP in dichloromethane (15 mL). This is followed by the dropwise addition of TEA (0.6 mL, 4.27 mmol). The reaction is stirred overnight. The reaction mixture is diluted with dichloromethane (50 mL), washed with aqueous HCl (10 mL 0.5 N) then saturated NaHCO₃ (10 mL) and brine (10 mL). The sample is dried over NaSO₄, filtered and concentrated in vacuo. Chromatography on silica gel using 30% ethyl acetate/hexanes provided 510 mg the title compound as a white solid. Recrystallization from ethyl acetate/hexanes yielded colorless needles. mp 186-188° C.; $[\alpha]_D^{25}$=−153.91° (1%, CHCl₃);

¹H NMR 500 MHz (DMSO-D6): δ 7.96 (d, 1H, J=7.33 Hz), 7.86 (m, 2H), 7.78 (d,1H, J=8.24 Hz), 7.53 (t, 1H, J=7.94 Hz), 7.22 (t, 1H, J=7.48 Hz), 7.12 (m, 2H), 6.79 (t, 1H, J=7.49 Hz), 6.01 (m, 4H), 4.01 (s, 3H), 3.68 (s, 6H), 3.05 (brs, 4H), 1.63 (s, 3H) (ESI) m/z 550 ([M+H]+); Anal. calcd for $C_{34}H_{35}N_3O_4$: C,74.29; H,6.42; N,7.64. Found: C,74.10; H,6.35; N,7.87.

Example 5

(S,S)-3-(2-methoxyphenyl)-2-methyl-3-(1-naphthyl)-2-({4-[3-(trifluoromethyl)phenyl]piperidin-1-yl}carbonyl)propanenitrile The title compound was prepared in 75% yield according to Example 4 using 4-(3-trifluoromethyl-phenyl)-piperidine. Recrystallization from ethyl acetate/hexane yielded white crystals. mp 123-127° C.; $[\alpha]_D^{25}$ =−144.4° (1%, CHCl₃);

¹H NMR 500 MHz (DMSO-D6): δ 8.02 (d, 1H, J=7.03 Hz), 7.88 (m, 2H), 7.82 (d, 1H, J=8.25 Hz), 7.56 (t, 1H, J=7.79 Hz), 7.51 (brm, 2H), 7.42 (d, 1H, J=7.48 Hz), 7.42 (quin, 1H J=3.51 Hz), 7.23 (t, 1H, J=7.03 Hz), 7.14 (m, 2H), 6.80 (t, 1H, J=7.48 Hz), 6.02 (s, 1H), 4.37 (brm, 2H), 4.01 (s, 3H), 2.88 (brn, 2H), 1.66 (s, 3H) MS (ESI) m/z 557 ([M+H]+); Anal. calcd for $C_{34}H_{31}F_3N_2O_2$: C,73.35; H,5.61; N,5.03. Found: C,73.99; H,6.00; N,4.72

Example 6

Isolated Rat Heart

Methods

The compounds of examples 2 and 3 were tested against vehicle (DMSO) in perfused isolated male rat hearts. Male rats 3 months old were anesthetized with sodium-pentobarbital and hearts were removed and mounted on a Langendorff apparatus. In this paradigm isolated hearts were perfused through an aortic cannula with a modified Krebs-Henseleit buffer equilibrated with 95% $O_2$ and 5% $CO_2$ at a constant pressure of 58 mmHg. Hearts were maintained at 37° C. throughout the experiments and temperature was continuously monitored with an IT-18 thermocouple microprobe inserted into the left ventricle (PhysiTemp, Clifton, N.J.). Flow rate was monitored with a flow probe and small animal flow meter (T206) from Transonic Systems Incorporated, Ithaca, N.Y. Hearts were perfused for 5 minutes with no additions followed by perfusion with vehicle or test compound which were continuously perfused throughout the remaining steps of the experiments. After 20 minutes the hearts were exposed to 100 nM isoproterenol for 5 minutes followed by 15 minutes global ischemia which was achieved by turning off the perfusion pump. After ischemia, hearts were reperfused at a constant flow rate for 50 minutes. This flow rate was equivalent to the rate used before ischemia to maintain 58 mmHg.

To assess ischemic damage, the change in left ventricular diastolic pressure was continually monitored using a fluid filled latex balloon inserted into the left ventricle through the left atrium. The diastolic pressure was initially adjusted to 5 mmHg. The pressure signals were recorded with a Grass Polygraph.

The release of creatine kinase (CK) enzyme activity from the hearts was also measured as a marker of cardiac damage. Fractions of perfusate were collected before ischemia and every 5 minutes during reperfusion. CK enzyme activity released from the hearts was determined in the perfusate fractions using CK reagent as recommended by the supplier (Sigma Diagnostics, St. Louis, Mo.). Standard curves for CK activity were made for each assay using human CK Accutrol Serum Standards from Sigma Diagnostics.

Figure 2:
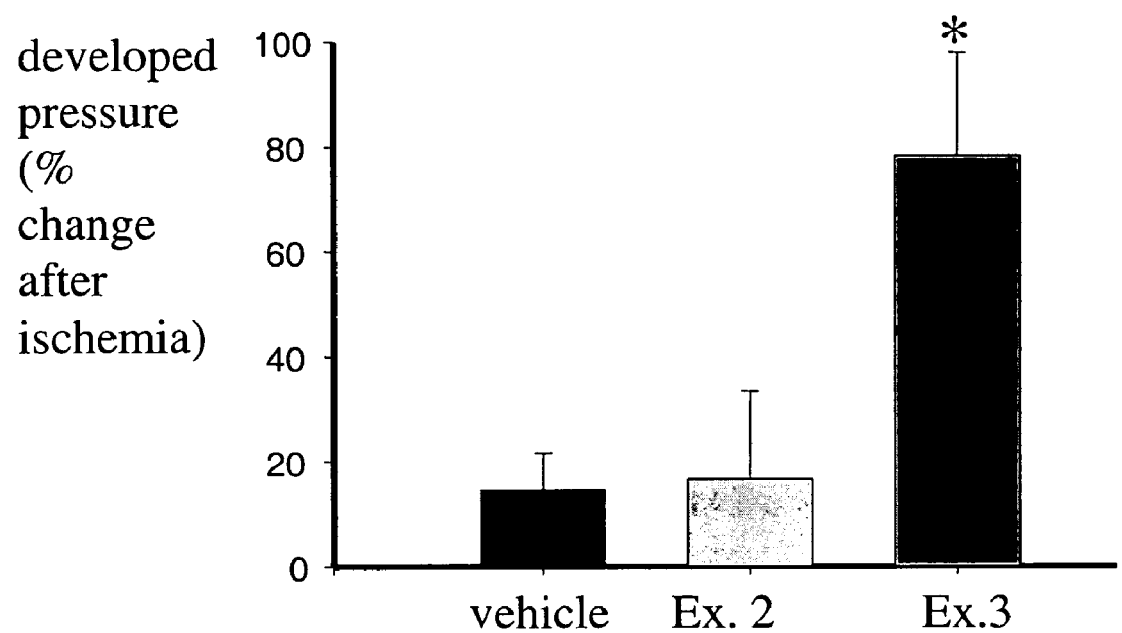
FIG. 2 shows the effect of tThe compounds of examples 2 and 3 on the recovery of cardiac function following ischemia-reperfusion. Left ventricular developed pressure at the end of the reperfusion phase is expressed as a percent of the developed pressure before ischemia. The compound of example 3 (n=8) treatment significantly attenuated the loss of developed pressure in comparison to vehicle (n=17) treated hearts following ischemia-reperfusion, *$p<0.01$.

In hearts perfused with vehicle and subjected to 15 minutes of ischemia and 50 minutes of reperfusion, left ventricular diastolic pressure increased by 29 mmHg (FIG. 1). In vehicle treated hearts there was also an 85% loss in developed pressure (FIG. 2). In hearts treated with luM of the compound of example 3 the increase in diastolic pressure after ischemia-reperfusion was significantly attenuated, 11 mmHg, in comparison to vehicle (FIG. 1). Treatment with the compound of example 2 also caused a significant 78% recovery in developed pressure following ischemia-reperfusion (FIG. 2). Treatment of hearts with 1 uM of the compound of example 2 did not significantly effect diastolic and developed pressures in comparison to vehicle (FIG. 1, 2).

Figure 3:
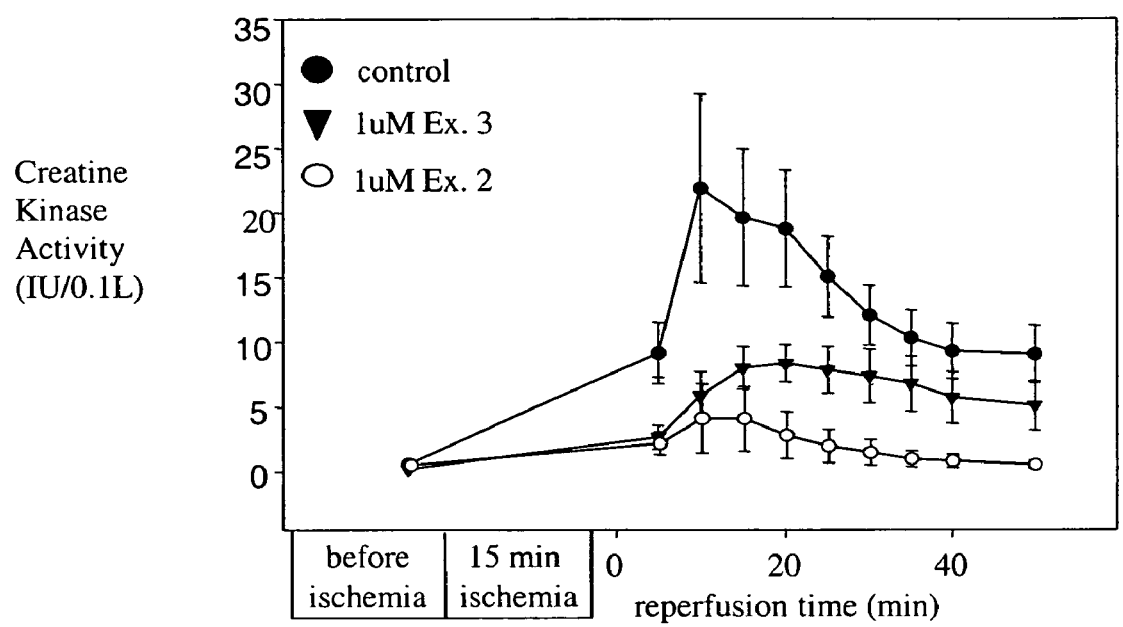
FIG. 3 shows the effect of the compounds of examples 2 and 3 on creatine kinase activity released from hearts after ischemia. CK activity released from hearts before and after ischemia is shown for the vehicle group (closed circles), the compound of example 3 treatment group (triangles) and the compound of example 2 treatment group (open circles). The average CK value for each heart during the reperfusion phase was used to compare each treatment group. Both treatment groups significantly reduced the release of creatine kinase. $p<0.05$ for the treatment groups verses vehicle group.

Following ischemia in hearts treated with vehicle, CK enzyme was released from the hearts during the reperfusion phase (FIG. 3). Treatment of hearts with 1 uM of the compound of example 3 or 1 uM of the compound of example 2 caused significant decreases in the release of CK following ischemia (FIG. 3).

Example 7

In Vivo Rat Heart

Methods

A rat in vivo model was used to evaluate effects of experimental compounds on ischemia-reperfusion in the left ventricle. Adult ovariectomized female Sprague Dawley rats (>6 weeks) were used. All experimental procedures were performed under general anesthesia with a combination of ketamine and xylazine. Rats were placed on a heating pad and ventilated using a rodent ventilator. The chest was clipped free of hair, disinfected with Betadine and rinsed with alcohol. A small incision was made through skin and underlying muscles between $4^{th}$ and $5^{th}$ ribs in the left chest. The ribs were gently spread and the heart was exposed. A surgical suture was placed under the left coronary artery. The artery was occluded by tightening the suture for 30 minutes to induce myocardial ischemia and then re-opened for the 2 hour reperfusion period. Vehicle or the compound of example 2 or 3(1 mg/kg) were intravenously administered 25 minutes after initiation of ischemia, i.e. 5 minutes before reperfusion. At the end of reperfusion, hearts were harvested, perfused with Evans Blue, sectioned and stained with 2,3,5-triphenyltetrazolium chloride. Each section was digitally imaged. Infarct size and area at risk were measured and statistically analyzed.

Figure 4:
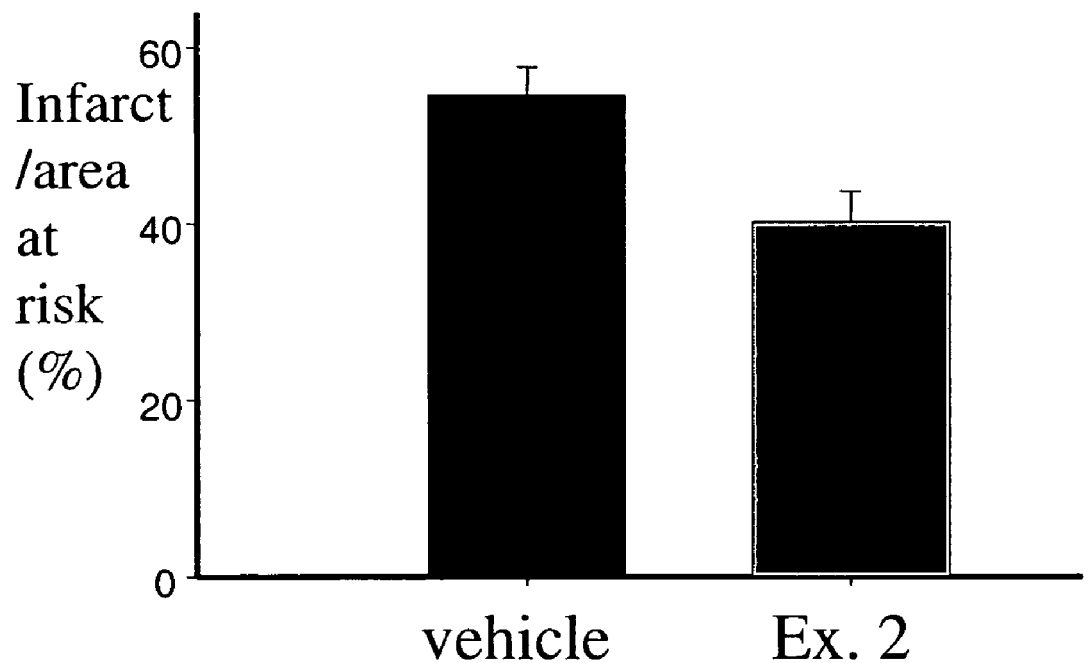
FIG. 4 shows that the compound of example 2 significantly reduced ischemia/reperfusion-induced myocardial infarction in adult ovariectomized female rats as compared with vehicle-treated animals. *$p<0.01$, n=10 per group.

As shown in FIG. 4, occlusion of left coronary artery followed by reperfusion resulted in myocardial infarction in both the vehicle and the compound of example 2 (1 mg/kg, iv) treated rats. However, the infarct size was significantly reduced in the compound of example 2 treated rats (40.2±3.5%) compared to the vehicle-treated animals (54.6±3.2%).

Figure 5:
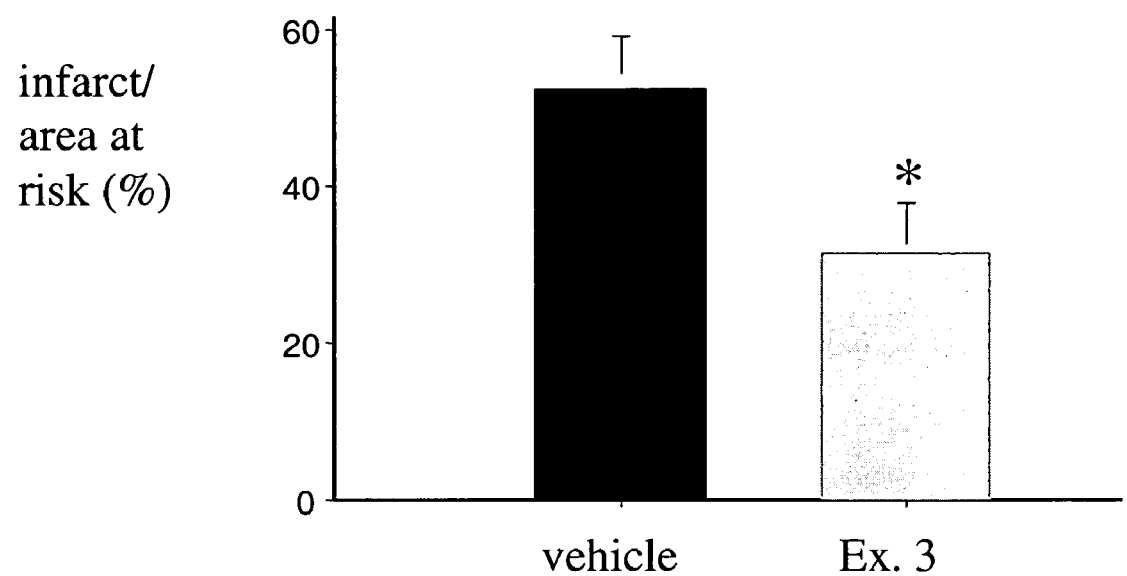
FIG. 5 shows the effects of the compound of example 3 on ischemia/reperfusion-induced myocardial infarction. The rats treated with the compound of example 3 had significantly less myocardial infarction as compared with the vehicle group. *$p<0.01$, n=12 in each group.

In a second study (FIG. 5) using the same model, myocardial infarction was also observed in the vehicle and the compound of example 3 (1 mg/kg, iv) treated rats. There was a significant difference in the infarct size between the vehicle and the compound of example 3 treatments, i.e. 54.4±4.7% and 32.6±5.2% (Mean±SEM), respectively.

Example 8

In Vivo Rabbit Heart

Ovariectomized female New Zealand White rabbits were anesthetized with a mixture of xylazine (3 mg/kg) and ketamine (35 mg/kg) administered IM, followed by an IV injection of sodium pentobarbital (15 mg/kg). An endotracheal tube was inserted and animals were positive pressure ventilated with room air. A Millar catheter micro-tip pressure transducer was inserted through the left carotid artery and positioned above the aortic valves to monitor aortic blood pressure. A lead II electrocardiogram was monitored throughout the experiment. A left thoracotomy and pericardiotomy were performed. The compounds of example 2 or 3 or vehicle (20% DMSO:80% PEG-200) were administered IV through the left jugular vein at 1 mg/kg 15 minutes after the thoracotomy was performed and 30 minutes before the induction of regional myocardial ischemia. A silk suture was passed behind the left anterior descending coronary artery and secured against polyethylene tubing for 30 minutes- (ischemic period). Regional myocardial ischemia was verified by cyanosis in the region of the occluded vessel and by ST-segment elevation like changes in the electrocardiogram. The hearts were then reperfused for 4 hours.

To determine infarct size the heart was removed, cannulated through the aorta and perfused with Krebs-Henseleit buffer followed by perfilsion with 1% triphenyltetrazolium chloride (TTC). The left anterior descending coronary artery was re-occluded with a suture and 0.25% Evans Blue was perfused through the heart. The heart was cut into transverse sections and the area of the left ventricle, area at risk and the infarct area were traced and analyzed using Adobe PhotoShop Software. The infarct size is expressed as a percentage of the area at risk.

Figure 6:
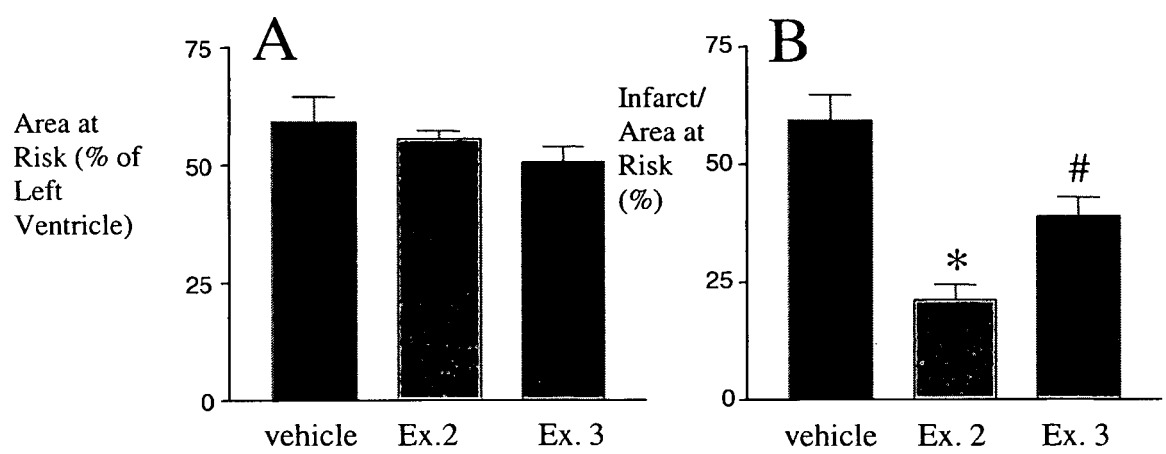
FIG. 6 shows the effect of the compound of examples 2 and 3 on infarct size following ischemia-reperfusion in rabbit heart. The compounds of examples 2 and 3 at 1 mg/kg or vehicle were administered IV 30 minutes before the induction of ischemia. The area at risk is expressed as percent of left ventricle (A) and the infarct size is expressed as a percent of the area at risk (B). n=5 for each group. *p<0.001, +p<0.005 for treatment verses vehicle.

In rabbits, occlusion of the left anterior descending coronary artery for 30 minutes caused infarction in the left ventricle. When The compounds of examples 2 and 3 were administered IV at 1 mg/kg 30 minutes before induction of ischemia they did not have an effect on the size of the area at risk relative to the area of the left ventricle (FIG. 6A). Administration of The compounds of examples 2 and 3 both significantly reduced infarct size in comparison to vehicle administration (FIG. 6B). The ischemic area relative to the area at risk was 59% for the vehicle group, 39% for the compound of example 3 treatment group and 21% for the compound of example 2 treatment group.

As described in examples 6-9, novel ER ligands were tested in three models of myocardial ischemia-reperftision injury: I) the isolated rat heart, II.) the in vivo rat heart and III.) the in vivo rabbit heart. The compound of example 3 showed cardioprotective activity on all the endpoints in the three models. The compound of example 2 did not have activity on the functional end points, diastolic pressure and developed pressure, in the isolated heart model (Model I). However in the isolated heart, the compound of example 2 attenuated the release of CK activity following ischemia indicating decreased tissue damage. Furthermore, the compound of example 2 had activity on infarct size in both the rat and rabbit in vivo MI models. 17β-estradiol was found to be protective in similar myocardial ischemia-reperfusion models. However in contrast to the known effects of 17β-estradiol, the compound of example 2 and the compound of example 3 have no activity in the uterus or breast. The results with The compounds of examples 2 and 3 in the myocardial ischemia-reperfusion models demonstrate that these compounds could be used to inhibit the development of ischemic damage during MI and during procedures that cause ischemia.

All patents, patent applications, and publications disclosed herein are incorporated by reference into the specification in their entirety.

What is claimed is:

1. A method of treatment of myocardial ischemia-reperfusion injury comprising the steps:
   identifying a person in need of treatment of myocardial ischemia-reperfusion injury; and
   administering to said person a therapeutically effective amount of a ligand of the structure

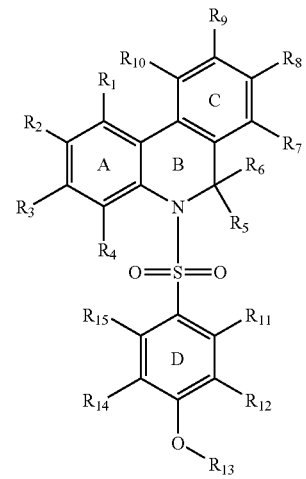

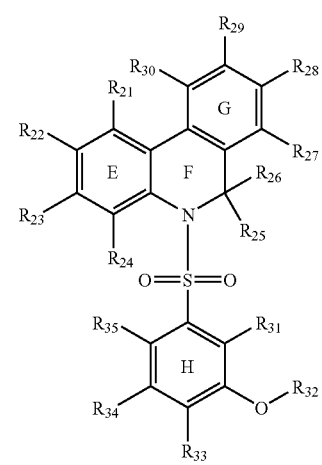

wherein
$R_1$, $R_2$, $R_3$, $R_4$, $R_7$, $R_8$, $R_9$, $R_{10}$, $R_{11}$, $R_{12}$, $R_{14}$, and $R_{15}$ are each, independently, hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)═NR, cyano, nitro, halogen, —OR, —SR, —SO$_3$R, —S(O)$_2$N(R)$_2$, —C(O)R, —C(R)═N—OR, —C(NH$_2$)═NR, —CO$_2$R, —OC(O)R, or —C(O)N(R)$_2$; or are taken together with either $R_{p+1}$ or $R_{p-1}$ linked with an -alkylene-, or —X-alkylene- group;

$R_5$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, —CR(O), —CO$_2$R, or —C(O)N(R)$_2$; or $R_5$ may be taken together with either $R_6$ or $R_7$ and linked with an -alkylene- or —X-alkylene- group;

$R_6$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, —CR(O), —CO$_2$R, or —C(O)N(R)$_2$; or $R_6$ may be taken together with either $R_5$ or $R_7$ and linked with an -alkylene- or —X-alkylene- group;

$R_{13}$ is R, $R_{17}$—X—$R_{16}$—, $R_{17}$—S(O)—, $R_{17}$—S(O)$_2$—, —SO$_3$R, —S(O)$_2$N(R)$_2$, or D-glucuronidate;

$R_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-(C$_2$-C$_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene-group;

X is O, —NR—, —S(O)$_m$—, —C(O)—, —OC(O)—, —C(O)O—, —NRC(O)—, or —C(O)NR—;

m is 0, 1, or 2;

p is 2, 3, 6, 7, 8, 9, 12, 13, or 14;

$R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are, independently, hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, $R_{17}$—S(O)—, $R_{17}$—S(O)$_2$—, $R_{17}$SO$_3$—, $R_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either $R_{q+1}$ or $R_{q-1}$ linked with an -alkylene-, or —Y-alkylene- group;

$R_{25}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{25}$ may be taken together with either $R_{26}$ or $R_{27}$ and linked with an -alkylene- or —Y-alkylene- group;

$R_{26}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{26}$ may be taken together with either $R_{25}$ or $R_{27}$ and linked with an -alkylene- or —Y-alkylene- group;

$R_{32}$ is R, $R_{17}$—Y—$R_{16}$—, $R_{17}$—S(O)—, $R_{17}$—S(O)$_2$—, —SO$_3$R, —S(O)$_2$N(R)$_2$, or D-glucuronidate;

Y is O, —NR—, —S(O)$_n$—, —C(O)—, —OC(O)—, —C(O)O—, —NRC(O)—, or —C(O)NR—;

n is 0, 1, or 2;

q is 22, 23, 26, 27, 28, 29, 32, 33, or 34;

or a pharmaceutically acceptable salt thereof.

2. The method of claim 1, wherein the ligand is of formula (I).

3. The method of claim 2, wherein $R_{13}$ is hydrogen.

4. The method of claim 3, wherein $R_1$, $R_2$, $R_3$, $R_4$, $R_7$, $R_8$, $R_9$, $R_{10}$, $R_{11}$, $R_{12}$, $R_{14}$, and $R_{15}$ are each, independently, hydrogen, $R_{17}$, aryl-$R_{16}$-, $R_{17}$—X—$R_{16}$—, hydroxyalkyl, HO—$R_{16}$—, halogen, —OR, —COR, or —CO$_2$R;

$R_5$ and $R_6$ are each, independently, hydrogen or $R_{17}$;

$R_{16}$ is -alkylene-;

$R_{17}$ is alkyl, aryl, heteroaryl, or perfluoroalkyl;

R is hydrogen or alkyl.

5. The method of claim 1, wherein the ligand is of formula (II).

6. The method of claim 5, wherein $R_{32}$ is hydrogen.

7. The method of claim 6, wherein $R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are each, independently, hydrogen, $R_{17}$, aryl-$R_{16}$—, $R_{17}$—Y—$R_{16}$—, hydroxyalkyl, HO—$R_{16}$—, halogen, —OR, —COR, or —CO$_2$R;

$R_{25}$ and $R_{26}$ are each, independently, hydrogen or $R_{17}$;

$R_{16}$ is -alkylene-;

$R_{17}$ is alkyl, aryl, heteroaryl, or perfluoroalkyl;

R is hydrogen or alkyl.

8. The method of claim 1, where the ligand is

4-[(6-methylphenanthridin-5(6H)-yl)sulfonyl]phenol;

4-{[(S)-6-methylphenanthridin-5(6H)-yl]sulfonyl}phenol;

4-{[(R)-6-methylphenanthridin-5(6H)-yl]sulfonyl}phenol;

4-[(2-bromo-6-methylphenanthridin-5(6H)-yl)sulfonyl]phenol;

2-methyl-4-[(6-methylphenanthridin-5(6H)-yl)sulfonyl]phenol;

4-[(2-bromo-6-methylphenanthridin-5(6H)-yl)sulfonyl]-2-methylphenol;

4-[(6-butylphenanthridin-5(6H)-yl)sulfonyl]phenol;

4-[(2-bromo-6-butylphenanthridin-5(6H)-yl)sulfonyl]phenol;

4-[(6-phenylphenanthridin-5(6H)-yl)sulfonyl]phenol;

4-{[(S)-6-phenylphenanthridin-5(6H)-yl]sulfonyl}phenol;

4-{[(R)-6-phenylphenanthridin-5(6H)-yl]sulfonyl}phenol;

4-[(2-bromo-6-phenylphenanthridin-5(6H)-yl)sulfonyl]phenol;

2-bromo-4-[(2-bromo-6-phenylphenanthridin-5(6H)-yl)sulfonyl]phenol;

4-[(6-tert-butylphenanthridin-5(6H)-yl)sulfonyl]phenol;

4-{[(R)-6-tert-butylphenanthridin-5(6H)-yl]sulfonyl}phenol;

4-{[(S)-6-tert-butylphenanthridin-5(6H)-yl]sulfonyl}phenol;

4-[(2-bromo-6-tert-butylphenanthridin-5(6H)-yl)sulfonyl]phenol;

4-[(6-ethylphenanthridin-5(6H)-yl)sulfonyl]phenol;

4-[(2-bromo-6-ethylphenanthridin-5 (6H)-yl)sulfonyl]phenol;

4-[(6-ethylphenanthridin-5(6H)-yl)sulfonyl]-2-methylphenol;

4-[(2-bromo-6-ethylphenanthridin-5(6H)-yl)sulfonyl]-2-methylphenol;

4-{[(S*)-6-[(R*)-1-methylpropyl]phenanthridin-5(6H)-yl]sulfonyl}phenol;

4-[(6-methylphenanthridin-5(6H)-yl)sulfonyl]benzene-1,2-diol;

2-hydroxy-5-[(6-methylphenanthridin-5(6H)-yl)sulfonyl]benzoic acid;

ethyl 2-ethoxy-5-[(6-methylphenanthridin-5(6H)-yl)sulfonyl]benzoate;

2-(hydroxymethyl)-4-[(6-methylphenanthridin-5(6H)-yl)sulfonyl]phenol;

2-hydroxy-5-[(6-methylphenanthridin-5(6H)-yl)sulfonyl]benzaldehyde;

4-[(6-ethyl-2-thien-3-ylphenanthridin-5(6H)-yl)sulfonyl]phenol;

4-{[6-ethyl-2-(3-methoxyphenyl)phenanthridin-5(6H)-yl]sulfonyl}phenol;

3-{6-ethyl-5-[(4-hydroxyphenyl)sulfonyl]-5,6-dihydrophenanthridin-2-yl}phenol;

4-[(2-dibenzo [b,d]furan-4-yl-6-ethylphenanthridin-5 (6H)-yl)sulfonyl]phenol;
4-[(8-fluoro-6-methylphenanthridin-5(6H)-yl)sulfonyl] phenol;
4-{[(S)-8-fluoro-6-methylphenanthridin-5(6H)-yl] sulfonyl}phenol;
4-{[(R)-8-fluoro-6-methylphenanthridin-5(6H)-yl] sulfonyl}phenol;
4-[(8-fluoro-6-methylphenanthridin-5(6H)-yl)sulfonyl]-2-methylphenol;
5-[(4-hydroxyphenyl)sulfonyl]-6-methyl-5,6-dihydro-phenanthridin-9-ol;
5-[(4-hydroxy-3-methylphenyl)sulfonyl]-6-methyl-5,6-dihydrophenanthridin-9-ol;
5-[(4-hydroxy-3-methylphenyl)sulfonyl]-6-methyl-5,6-dihydrophenanthridin-7-ol;
5-[(4-hydroxyphenyl)sulfonyl]-6-methyl-5,6-dihydro-phenanthridin-7-ol;
4-[(6-ethyl-8-fluorophenanthridin-5(6H)-yl)sulfonyl] phenol;
4-[(6-ethyl-8-fluorophenanthridin-5(6H)-yl)sulfonyl]-2-methylphenol;
4-[(6-ethyl-7-methylphenanthridin-5(6H)-yl)sulfonyl] phenol;
4-[(6-ethyl-9-methylphenanthridin-5(6H)-yl)sulfonyl] phenol;
4-[(2-bromo-6-ethyl-8-fluorophenanthridin-5(6H)-yl)sul-fonyl]phenol;
4-[(2-bromo-8-fluoro-6-methylphenanthridin-5(6H)-yl) sulfonyl]phenol;
2-chloro-4-[(6-ethyl-8-fluorophenanthridin-5(6H)-yl)sul-fonyl]phenol;
4-[(6-ethyl-8-fluoro-2-phenylphenanthridin-5(6H)-yl) sulfonyl]phenol;
3-[(8-fluoro-6-methylphenanthridin-5(6H)-yl)sulfonyl] phenol;
2-fluoro-4-[(8-fluoro-6-methylphenanthridin-5(6H)-yl) sulfonyl]phenol;
4-[(8-fluoro-6-methylphenanthridin-5(6H)-yl)sulfonyl] benzene-1,2-diol;
4-[(6-ethyl-8-fluoro-2-methylphenanthridin-5(6H)-yl) sulfonyl]phenol;
4-[(6-ethyl-8-fluoro-2-thien-3-ylphenanthridin-5(6H)-yl) sulfonyl]phenol;
4-[(6-ethyl-8-fluorophenanthridin-5(6H)-yl)sulfonyl] phenyl 3,3-dimethylbutanoate;
4-[(6-ethyl-8-fluorophenanthridin-5(6H)-yl)sulfonyl] phenyl propionate;
4-[(6-ethyl-8-fluorophenanthridin-5(6H)-yl)sulfonyl] phenyl benzoate;
2-fluoro-4-[(6-methylphenanthridin-5(6H)-yl)sulfonyl] phenol;
4-[(2-bromo-6-methylphenanthridin-5(6H)-yl)sulfonyl]-2-fluorophenol;
4-[(6-methylphenanthridin-5(6H)-yl)sulfonyl]-2-(trifluo-romethyl)phenol;
2,6-dimethyl-4-[(6-methylphenanthridin-5(6H)-yl)sulfo-nyl]phenol;
4-[(6,8-dimethylphenanthridin-5(6H)-yl)sulfonyl]phenol;
4-[(8-chloro-6-methylphenanthridin-5(6H)-yl)sulfonyl] phenol;
4-[(2-bromo-8-chloro-6-methylphenanthridin-5(6H)-yl) sulfonyl]phenol;
2-{6-ethyl-5-[(4-hydroxyphenyl)sulfonyl]-5,6-dihydro-phenanthridin-2-yl}phenol;
4-{[6-ethyl-2-[4-(methylthio)phenyl]phenanthridin-5 (6H)-yl]sulfonyl}phenol;
4-{[6-ethyl-2-[(E)-2-phenylethenyl]phenanthridin-5 (6H)-yl]sulfonyl}phenol;
4-{[2-(1,1'-biphenyl-4-yl)-6-ethylphenanthridin-5(6H)-yl]sulfonyl}phenol;
4-{[2-(3-chlorophenyl)-6-ethylphenanthridin-5(6H)-yl] sulfonyl}phenol;
4-[(6-ethyl-2-quinolin-8-ylphenanthridin-5(6H)-yl)sulfo-nyl]phenol;
4-[(6-ethyl-2-phenylphenanthridin-5(6H)-yl)sulfonyl] phenol;
4-{[6-ethyl-2-(2-methylphenyl)phenanthridin-5(6H)-yl] sulfonyl}phenol;
4-[(6-ethyl-2-thianthren-1-ylphenanthridin-5(6H)-yl)sul-fonyl]phenol;
4-{[2-(1-benzofuran-2-yl)-6-ethylphenanthridin-5(6H)-yl]sulfonyl}phenol;
4-{[6-ethyl-2-(4-hydroxyphenyl)phenanthridin-5(6H)-yl] sulfonyl}phenol;
4-{[2-(2-chlorophenyl)-6-ethylphenanthridin-5(6H)-yl] sulfonyl}phenol;
4-{[6-ethyl-2-(4-ethylphenyl)phenanthridin-5(6H)-yl] sulfonyl}phenol;
1-(5-{6-ethyl-5-[(4-hydroxyphenyl)sulfonyl]-5,6-dihy-drophenanthridin-2-yl}thien-2-yl)ethanone;
5-{6-ethyl-5-[(4-hydroxyphenyl)sulfonyl]-5,6-dihydro-phenanthridin-2-yl}pyrimidine-2,4-diol;
4-{[6-ethyl-2-(2-hydroxyphenyl)phenanthridin-5(6H)-yl] sulfonyl}-2-methylphenol;
4-[(6-ethyl-2-thien-3-ylphenanthridin-5(6H)-yl)sulfo-nyl]-2-methylphenol;
4-{[6-ethyl-2-[4-(methylthio)phenyl]phenanthridin-5 (6H)-yl]sulfonyl}-2-methylphenol;
4-{[6-ethyl-2-[(E)-2-phenylethenyl]phenanthridin-5 (6H)-yl]sulfonyl}-2-methylphenol;
4-{6-ethyl-5-[(4-hydroxy-3-methylphenyl)sulfonyl]-5,6-dihydrophenanthridin-2-yl}benzene-1,2-diol;
4-{[2-(1,1'-biphenyl-4-yl)-6-ethylphenanthridin-5(6H)-yl]sulfonyl}-2-methylphenol;
4-{[6-ethyl-2-(3-hydroxyphenyl)phenanthridin-5(6H)-yl]sulfonyl}-2-methylphenol;
4-{[2-(3-chlorophenyl)-6-ethylphenanthridin-5(6H)-yl] sulfonyl}-2-methylphenol;
4-{[6-ethyl-2-[(E)-hept-1-enyl]phenanthridin-5(6H)-yl] sulfonyl}-2-methylphenol;
4-[(6-ethyl-2-pyridin-4-ylphenanthridin-5(6H)-yl)sulfo-nyl]-2-methylphenol;
4-[(6-ethyl-2-quinolin-8-ylphenanthridin-5(6H)-yl)sulfo-nyl]-2-methylphenol;
4-{[6-ethyl-2-(2-methylphenyl)phenanthridin-5(6H)-yl] sulfonyl}-2-methylphenol;
4-{[2-(1-benzothien-2-yl)-6-ethylphenanthridin-5(6H)-yl]sulfonyl}-2-methylphenol;
4-{[2-(1-benzothien-3-yl)-6-ethylphenanthridin-5(6H)-yl]sulfonyl}-2-methylphenol;
4-[(2-dibenzo [b,d]furan-4-yl-6-ethylphenanthridin-5 (6H)-yl)sulfonyl]-2-methylphenol;
4-{[2-(1-benzofuran-2-yl)-6-ethylphenanthridin-5(6H)-yl]sulfonyl}-2-methylphenol;
4-{[6-ethyl-2-(4-hydroxyphenyl)phenanthridin-5(6H)-yl] sulfonyl}-2-methylphenol;
4-{[2-(2-chlorophenyl)-6-ethylphenanthridin-5(6H)-yl] sulfonyl}-2-methylphenol;

4-{[6-ethyl-2-(4-ethylphenyl)phenanthridin-5(6H)-yl]
sulfonyl}-2-methylphenol;

1-(5-{6-ethyl-5-[(4-hydroxy-3-methylphenyl)sulfonyl]-5,
6-dihydrophenanthridin-2-yl}thien-2-yl)ethanone;

5-{6-ethyl-5-[(4-hydroxy-3-methylphenyl)sulfonyl]-5,6-
dihydrophenanthridin-2-yl}pyrimidine-2,4-diol, or a pharmaceutically acceptable salt thereof.

9. A method of treatment of myocardial ischemia-reperfusion injury comprising the steps:

identifying a person in need of treatment or prevention of myocardial ischemia-reperfusion injury; and administering to said person a therapeutically effective amount of a ligand of the formula:

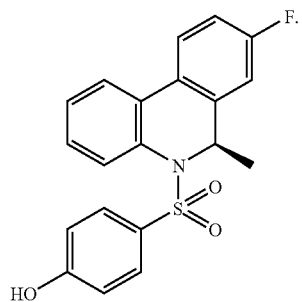

* * * * *